(12) United States Patent
Cheng

(10) Patent No.: US 11,965,889 B2
(45) Date of Patent: Apr. 23, 2024

(54) LYSINE MONOMETHYLATED DERIVATIVE AND CORRESPONDING ANTIBODY AND USE THEREOF

(71) Applicant: PMT Biolabs Inc, Hangzhou (CN)

(72) Inventor: Zhongyi Cheng, Hangzhou (CN)

(73) Assignee: PMT BIOLABS INC, Hangzhou (CN)

( * ) Notice: Subject to any disclaimer, the term of this patent is extended or adjusted under 35 U.S.C. 154(b) by 634 days.

(21) Appl. No.: 16/749,036

(22) Filed: Jan. 22, 2020

(65) Prior Publication Data

US 2020/0150129 A1 May 14, 2020

Related U.S. Application Data

(63) Continuation of application No. 15/323,873, filed as application No. PCT/CN2015/084391 on Jul. 18, 2015, now Pat. No. 10,551,390.

(30) Foreign Application Priority Data

Jul. 25, 2014 (CN) .......................... 201410359860.4
Jul. 25, 2014 (CN) .......................... 201410360062.3

(51) Int. Cl.
| | |
|---|---|
| C07K 16/18 | (2006.01) |
| C07C 233/47 | (2006.01) |
| C07K 7/08 | (2006.01) |
| C07K 14/435 | (2006.01) |
| C07K 16/44 | (2006.01) |
| G01N 33/53 | (2006.01) |
| G01N 33/68 | (2006.01) |

(52) U.S. Cl.
CPC ....... *G01N 33/6848* (2013.01); *C07C 233/47* (2013.01); *C07K 7/08* (2013.01); *C07K 14/43504* (2013.01); *C07K 16/18* (2013.01); *C07K 16/44* (2013.01); *G01N 33/53* (2013.01); *C07K 2317/34* (2013.01); *C07K 2317/92* (2013.01); *G01N 2440/12* (2013.01)

(58) Field of Classification Search
CPC ...... C07C 233/47; C07K 16/44; C07K 16/18; C07K 7/08; C07K 14/43504; C07K 2317/92; C07K 2317/34; G01N 33/53; G01N 33/6848; G01N 2440/12
See application file for complete search history.

(56) References Cited

U.S. PATENT DOCUMENTS 7,204,984 B2 * 4/2007 Komatsu ................ C07K 16/44
424/133.1

OTHER PUBLICATIONS

Komatsu et al. Four different clones of mouse anti-acetyllysine monoclonal antibodies having different recognition properties share a common immunoglobulin framework structure. Journal of Immunological Methods 2003, vol. 272, pp. 161-175. (Year: 2003).*
Iwabata et al. Proteomic analysis of organ-specific post-translational lysine-acetylation and -methylation in mice by use of anti-acetyllysine and -methyllysine mouse monoclonal antibodies. Proteomics 2005, vol. 5, pp. 4653-4664. (Year: 2005).*
Cao et al. Large-scale global identification of protein lysine methylation in vivo. Epigenetics 2013, vol. 8, No. 5, pp. 477-485. (Year: 2013).*

* cited by examiner

*Primary Examiner* — Shafiqul Haq
(74) *Attorney, Agent, or Firm* — Muncy, Geissler, Olds & Lowe, P.C.

(57) ABSTRACT

The present invention relates to artificially synthesized modified mono-methylated lysines and modified mono-methylated lysine derivatized polypeptides. The present invention also relates to production of a completely new antibody by using this modified mono-methylated lysine and modified mono-methylated lysine derivatized polypeptide as an antigen, this antibody can be used in recognizing and enriching the modified polypeptide after the lysine mono-methylated polypeptide being derivatized in vitro. By using this antibody, it is capable of detecting whether a mono-methylation modification is present in amino acids on the polypeptide sequence, the present invention also relates to a preparation method of said antibody. Moreover, the present invention also relates to a method for identifying and quantifying the lysine mono-methylated modified substrate in cell or tissue; more specifically, it belongs to identifying and quantifying the lysine mono-methylated modified substrate in cell or tissue by using proteomics approach of affinity enrichment for specific antibody and mass spectrometry.

1 Claim, 18 Drawing Sheets
Specification includes a Sequence Listing.

Carboxylic acid

RCOOH, R = alkyl or aryl, such as methyl, ethyl, propyl, iso-propyl, phenyl, heteroaryl etc.

Anhydride

R = alkyl, aryl, or heteroaryl, such as dash line is alkyl, aryl or heteroaryl, such as acyl chloride R = alkyl or aryl, such as R = alkyl or aryl, such as

| Name of gene | Modification sites identified by the present invention | Be reported or not? |
|---|---|---|
| ASH2L | K161 | No |
| BYSL | K4 | No |
| CDC5L | K164 | No |
| CXXC1 | K175 | No |
| EEF1A1P5 | K153,K164 | No, Yes |
| EIF2B1 | K144 | No |
| EZH2 | K734 | No |
| H3F3A | K27,K36 | Yes, Yes |
| HIST1H1E | K25 | Yes |
| HIST1H4A | K20 | Yes |
| HIST2H3A | K4 | Yes |
| HIST2H3A | K9 | Yes |
| HIST2H3A | K18 | Yes |
| HIST2H3A | K27,K36 | Yes, Yes |
| HIST2H3A | K79 | Yes |
| HNRNPC | K18 | No |
| HSP90AA1 | K614 | Yes |
| LASP1 | K38 | No |
| NOP14 | K5 | No |
| NUMA1 | K963 | No |
| POLR2B | K1044 | No |
| PRKDC | K2692 | No |
| RPL13 | K199 | No |
| RPL29 | K4 | No |
| RPL36A | K64 | No |
| SLC25A5 | K146 | No |
| STUB1 | K2 | No |
| SYMPK | K1149 | No |
| TXNRD1 | K37 | No |

FIG. 13

SEQUENCE LISTING

```
<160> NUMBER OF SEQ ID NOS: 29

<210> SEQ ID NO 1
<211> LENGTH: 46
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(21)
<223> OTHER INFORMATION: Xaa at positions 2-21 may be any amino acid
      among 19 types of common amino acids except for cysteine; and up
      to 19 of them maybe absent
<220> FEATURE:
<221> NAME/KEY: MISC_FEATURE
<222> LOCATION: (24)..(24)
<223> OTHER INFORMATION: modified monomethylated lysine
<220> FEATURE:
<221> NAME/KEY: MISC_FEATURE
<222> LOCATION: (27)..(46)
<223> OTHER INFORMATION: Xaa at positions 27-46 may be any amino acid
      among 19 types of common amino acids except for cysteine; and up
      to 19 of them maybe absent

<400> SEQUENCE: 1

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Gly Gly Xaa Gly Gly Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

<210> SEQ ID NO 2
<211> LENGTH: 15
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (11)..(11)
<223> OTHER INFORMATION: methyl propionylation, methyl acetylation or
      methyl butyryl modified lysines

<400> SEQUENCE: 2

Cys Glu Gly Arg Gly Asp Ser Gly Gly Gly Xaa Gly Gly Ser Gly
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: propionyl methylation modified lysine
```

-continued

<400> SEQUENCE: 3

Tyr Ser Gln Ala Asp Ala Leu Xaa Tyr Val Gly Ile Glu Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: 13CD3-labeled, propionyl methylation modified
      lysine

<400> SEQUENCE: 4

Tyr Ser Gln Ala Asp Ala Leu Xaa Val Tyr Gly Ile Glu Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: propionyl methylation modified lysine
<220> FEATURE:
<221> NAME/KEY: MISC_FEATURE
<222> LOCATION: (8)..(8)
<223> OTHER INFORMATION: propionyl modified lysine
<220> FEATURE:
<221> NAME/KEY: MISC_FEATURE
<222> LOCATION: (10)..(10)
<223> OTHER INFORMATION: propionyl modified lysine

<400> SEQUENCE: 5

Leu Ala Asn Thr Gln Gly Xaa Xaa Ala Xaa Arg
1               5                   10

<210> SEQ ID NO 6
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: lysine methyl residues

<400> SEQUENCE: 6

Leu Ala Asn Thr Gln Gly Xaa Lys
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: propionyl methylation modified lysine

<400> SEQUENCE: 7

```
Pro Val Xaa Gly Ala Tyr Arg
1               5

<210> SEQ ID NO 8
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: propionyl methylation lysine

<400> SEQUENCE: 8

Xaa Gly Gly Pro Asp Asp Arg
1               5

<210> SEQ ID NO 9
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: propionyl methylation modified lysine
<220> FEATURE:
<221> NAME/KEY: MISC_FEATURE
<222> LOCATION: (8)..(8)
<223> OTHER INFORMATION: propionyl modified lysine
<220> FEATURE:
<221> NAME/KEY: MISC_FEATURE
<222> LOCATION: (10)..(10)
<223> OTHER INFORMATION: propionyl modified lysine

<400> SEQUENCE: 9

Leu Ala Asn Thr Gln Gly Xaa Xaa Ala Xaa
1               5                   10

<210> SEQ ID NO 10
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: 13CD3-labeled methyl lysine residues

<400> SEQUENCE: 10

Leu Ala Asn Thr Gln Gly Xaa Lys
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (7)..(7)
<223> OTHER INFORMATION: methyl propionyl modified lysine
```

<400> SEQUENCE: 11

Cys Xaa Xaa Xaa Xaa Xaa
1               5

<210> SEQ ID NO 12
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: methyl propionyl modified lysine

<400> SEQUENCE: 12

Cys Glu Gly Arg Gly Asp Ser Gly Gly Gly Xaa Gly Gly Ser Gly
1               5                   10                  15

<210> SEQ ID NO 13
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: methyl propionyl modified lysine

<400> SEQUENCE: 13

Lys Leu His Xaa
1

<210> SEQ ID NO 14
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (7)..(7)
<223> OTHER INFORMATION: propionyl lysine
<220> FEATURE:
<221> NAME/KEY: MISC_FEATURE
<222> LOCATION: (8)..(12)
<223> OTHER INFORMATION: any amino acid of 19 common amino acids except
      for cysteine

<400> SEQUENCE: 14

Cys Xaa Xaa Xaa Xaa Xaa Xaa Xaa Xaa Xaa Xaa
1               5                   10

<210> SEQ ID NO 15
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: propionyl lysine

<400> SEQUENCE: 15

Cys Glu Gly Arg Gly Asp Ser Gly Gly Gly Xaa Gly Gly Ser Gly
1               5                   10                  15

<210> SEQ ID NO 16
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (7)..(7)
<223> OTHER INFORMATION: methyl ethoxylated lysine
<220> FEATURE:
<221> NAME/KEY: MISC_FEATURE
<222> LOCATION: (8)..(12)
<223> OTHER INFORMATION: any amino acid of 19 common amino acids except
      for cysteine

<400> SEQUENCE: 16

Cys Xaa Xaa Xaa Xaa Xaa Xaa Xaa Xaa Xaa Xaa Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: methyl ethoxylated lysine

<400> SEQUENCE: 17

Cys Glu Gly Arg Gly Asp Ser Gly Gly Gly Xaa
1               5                   10

<210> SEQ ID NO 18
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (7)..(7)
<223> OTHER INFORMATION: methyl butyryl lysine
<220> FEATURE:
<221> NAME/KEY: MISC_FEATURE
<222> LOCATION: (8)..(12)
<223> OTHER INFORMATION: any amino acid of 19 common amino acids except
      for cysteine

<400> SEQUENCE: 18

Cys Xaa Xaa Xaa Xaa Xaa Xaa Xaa Xaa Xaa Xaa Xaa
1               5                   10

<210> SEQ ID NO 19
<211> LENGTH: 11

```
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: methyl butyryl lysine

<400> SEQUENCE: 19

Cys Glu Gly Arg Gly Asp Ser Gly Gly Gly Xaa
1               5                   10

<210> SEQ ID NO 20
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (8)..(12)
<223> OTHER INFORMATION: any amino acid of 19 common amino acids except
      for cysteine

<400> SEQUENCE: 20

Cys Xaa Xaa Xaa Xaa Xaa Lys Xaa Xaa Xaa Xaa Xaa
1               5                   10

<210> SEQ ID NO 21
<211> LENGTH: 15
<212> TYPE: PRT
<213> ORGANISM: Artificial Sequence
<220> FEATURE:
<223> OTHER INFORMATION: synthetic

<400> SEQUENCE: 21

Cys Glu Gly Arg Gly Asp Ser Gly Gly Gly Lys Gly Gly Ser Gly
1               5                   10                  15

<210> SEQ ID NO 22
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(21)
<223> OTHER INFORMATION: Xaa at positions 2-21 is any amino acid of 19
      common amino acids except for cysteine, and up to 19 of them may
      be absent
<220> FEATURE:
<221> NAME/KEY: MISC_FEATURE
<222> LOCATION: (22)..(22)
<223> OTHER INFORMATION: modified monomethyllysine
<220> FEATURE:
<221> NAME/KEY: MISC_FEATURE
<222> LOCATION: (23)..(42)
<223> OTHER INFORMATION: Xaa at positions 23-42 is any amino acid of 19
      common amino acids except for cysteine, and up to 19 of them may
      be absent

<400> SEQUENCE: 22

Cys Xaa Xaa Xaa Xaa Xaa Xaa Xaa Xaa Xaa Xaa Xaa Xaa Xaa Xaa Xaa
1               5                   10                  15
```

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 23
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (7)..(7)
<223> OTHER INFORMATION: methyl propionyl lysine
<220> FEATURE:
<221> NAME/KEY: MISC_FEATURE
<222> LOCATION: (8)..(12)
<223> OTHER INFORMATION: any amino acid of 19 common amino acids except
      for cysteine

<400> SEQUENCE: 23

Cys Xaa Xaa Xaa Xaa Xaa Xaa Xaa Xaa Xaa Xaa Xaa
1               5                   10

<210> SEQ ID NO 24
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (7)..(7)
<223> OTHER INFORMATION: propionyl lysine
<220> FEATURE:
<221> NAME/KEY: MISC_FEATURE
<222> LOCATION: (8)..(12)
<223> OTHER INFORMATION: any amino acid of 19 common amino acids except
      for cysteine

<400> SEQUENCE: 24

Cys Xaa Xaa Xaa Xaa Xaa Xaa Xaa Xaa Xaa Xaa Xaa
1               5                   10

<210> SEQ ID NO 25
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (7)..(7)
<223> OTHER INFORMATION: butyryl lysine
<220> FEATURE:
<221> NAME/KEY: MISC_FEATURE
<222> LOCATION: (8)..(12)

```
<223> OTHER INFORMATION: any amino acid of 19 common amino acids except
      for cysteine

<400> SEQUENCE: 25

Cys Xaa Xaa Xaa Xaa Xaa Xaa Xaa Xaa Xaa Xaa Xaa
1               5                   10

<210> SEQ ID NO 26
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (7)..(7)
<223> OTHER INFORMATION: methyl lysine
<220> FEATURE:
<221> NAME/KEY: MISC_FEATURE
<222> LOCATION: (8)..(12)
<223> OTHER INFORMATION: any amino acid of 19 common amino acids except
      for cysteine

<400> SEQUENCE: 26

Cys Xaa Xaa Xaa Xaa Xaa Xaa Xaa Xaa Xaa Xaa Xaa
1               5                   10

<210> SEQ ID NO 27
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (7)..(7)
<223> OTHER INFORMATION: di-methylated lysine
<220> FEATURE:
<221> NAME/KEY: MISC_FEATURE
<222> LOCATION: (8)..(12)
<223> OTHER INFORMATION: any amino acid of 19 common amino acids except
      for cysteine

<400> SEQUENCE: 27

Cys Xaa Xaa Xaa Xaa Xaa Xaa Xaa Xaa Xaa Xaa Xaa
1               5                   10

<210> SEQ ID NO 28
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(6)
<223> OTHER INFORMATION: any amino acid of 19 common amino acids except
      for cysteine
<220> FEATURE:
<221> NAME/KEY: MISC_FEATURE
<222> LOCATION: (7)..(7)
<223> OTHER INFORMATION: tri-methylated lysine
<220> FEATURE:
```

```
<221> NAME/KEY: MISC_FEATURE
<222> LOCATION: (8)..(12)
<223> OTHER INFORMATION: any amino acid of 19 common amino acids except
      for cysteine

<400> SEQUENCE: 28

Cys Xaa Xaa Xaa Xaa Xaa Xaa Xaa Xaa Xaa Xaa Xaa
1               5                   10

<210> SEQ ID NO 29
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: monomethylated lysine

<400> SEQUENCE: 29

Leu Ala Asn Thr Gln Gly Xaa Lys Ala Lys Arg
1               5                   10
```

LYSINE MONOMETHYLATED DERIVATIVE AND CORRESPONDING ANTIBODY AND USE THEREOF

CROSS REFERENCE TO RELATED APPLICATION

This application is a continuation of U.S. application Ser. No. 15/323,873, filed Jan. 4, 2017. U.S. application Ser. No. 15/323,873 is a 35 U.S.C. § 371 national phase application of PCT/CN2015/084391, filed Jul. 18, 2015, which application claims the priority from China Patent Application No. 201410359860.4, filed Jul. 25, 2014, and China Patent Application No. 201410360062.3, filed Jul. 25, 2014. The content of each of these applications is incorporated by reference herein in its entirety.

FIELD OF THE INVENTION

The present invention relates to the field of antigen design, antigen preparation and production of antibody by using antigen; more specifically, the present invention relates to an artificially synthesized novel modified monomethylated lysine and modified monomethylated lysine derivatized polypeptide, as well as producing a completely new antibody by using this modified monomethylated lysine and modified monomethylated lysine derivatized polypeptide as antigen; the antibody may be used in identifying and enriching the modified polypeptide after the lysine monomethylated polypeptide being derivatized in vitro, and the present invention also relates to a preparation method of said antibody. On the other hand, the present invention belongs to the field of detection and diagnosis, specifically, it belongs to a method for identifying and quantifying the lysine monomethylated modified substrate in cells or tissues; more specifically, it belongs to identifying and quantifying the lysine monomethylated modified substrate in cells or tissues by using a proteomics approach of affinity enrichment of specific antibody and mass spectrum analysis.

BACKGROUND OF THE INVENTION

Modification of protein or polypeptide is a naturally occurring phenomenon in vivo, it is primarily that the amino acid residues constituting the polypeptide or protein are modified by some groups, then a series of life activities being regulated in vivo. Typically, the modification may be methylation, acetylation, phosphorylation modification etc. As important lysine methylation modifications, the type of modifications is divided into monomethylation, dimethylation or trimethylation modification (Cheng X, Zhang X. Mutat Res (2007)). How to effectively detect the presence of methylation modification in vivo, especially mono-methylation modification, can provide effective detection of some important diseases with a new method. Because some naturally occurring methylation modifications, such as abnormality of monomethylation modification, may result in some severe diseases such as cancer etc. (Yutaka Kondo et al., Mol Cell Biol. 23(1): 206-215(2003), Berdasco M et al., Proc Natl Acad Sci, 106: 21830-21835 (2009)).

Lysine methylation modification is a common way of protein modification. Under normal circumstances, detection of protein modification requires antibody specifically identifying the modification, e.g., the protein lysine acetylation modification may be identified by a lysine acetylated pan antibody (Kouzarides, T. Cell, 128, 693-705 (2007), Berger, S. L. Nature, 447, 407-412 (2007)). According to the bonding form of methyl group to lysine, the lysine methylation modification includes three forms of monomethylation, dimethylation and trimethylation. Correspondingly, the development of highly sensitive and highly specific lysine monomethylated, dimethylated and trimethylated antibodies is the premise of detection of the protein lysine methylation modification. (Barski, A. et al., Cell 129, 823-837 (2007); Rea, S. et al., Nature 406, 593-599 (2000)). At present, although successfully developed lysine dimethylated and trimethylated antibodies have been used in detection of lysine dimethylation or trimethylation modification, no successfully developed lysine monomethylated modified antibodies are used in detection of lysine monomethylation modification (Ziqian Liang et al., Proteome Science, Volume 6, (1) 6:2 (2008)). Since the lysine monomethylation modifying group is very small, having a molecular weight of only 15 Da, it is extremely difficult to induce a high immune response, moreover, the organic property of the monomethyl group further weakens immunogenicity of the lysine residues. These intrinsic properties result in great difficulty in antibody development in which the lysine monomethylated group is used as immunogen or the lysine monomethylated modified polypeptide is used as immunogen. Therefore, it is necessary to develop a completely new antibody used in detection of the lysine monomethylation modification.

Mono-, di- or tri-methylation modification may occur on ε-amino group sidechain of the protein lysine residues. In the past few decades, the biological studies on lysine methylation modification (Kme) were mainly focused on core histone. Previous studies showed a key role of such modification in structure and function of chromosome. Such modification state is regulated by two groups of enzymes having opposite catalytic functions, i.e. lysine methyltransferase and lysine demethylase. At present, more than 50 lysine methyltransferases and about 25 lysine demethylases have been found. Histone lysine methylation modification is associated with various diseases, such as cancer. Corresponding, the lysine methylation regulatory enzymes become a series of potential drug targets.

At present the protein post-translational modifications (PTMs) found in histone are all present in non-histone. In the identified lysine methylation regulatory enzymes, there are some non-nuclear targeting enzymes and newly found lysine methylation regulatory enzymes without using histone as substrate, this reveals that the lysine methylation should be widely distributed in non-histone. Identification of the protein substrate is the premise of determination of the protein post-translational modification function, history of the biological study of lysine methylation elaborates the importance of the premise very clearly. After combing our data with other people's data, it is found that that lysine acetylation substrate occurs in three study areas of chromosome structure, transcriptional regulation and metabolism, furthermore these areas overlap mutually in terms of substrate. Although the identification of the substrate for lysine acetylation modification is late, the studies on it indicate that lysine acetylation has synergistic effect in above-described three study areas. Similarly, the identification and quantification of lysine methylation modification group founded some downstream non-histone and signal pathway not being associated with chromosome, this lay a solid foundation for subsequent function study.

However, identification of lysine methylation substrate is not easy. Different from $^{32}P$ labelling for identifying phosphorylation modification, low radioactivity of $^{3}H$ or $^{14}C$ make the radioactive isotope detection method difficult to be realized in the identification of lysine methylation substrate.

In methylation, especially monomethylation (Kme1), only one very small structural group is introduced into its substrate, thus difference between the modified lysine group and the unmodified lysine group is slight, only a very small conformation is used for development of affinity antibody. If both of affinity and specificity are taken into account, development of methylation antibody (pan antibody) not being associated with sequence is a great challenge. As a result, because no suitable methylation peptide enrichment method provides peptide for the subsequent mass spectrum analysis, the identification process of the lysine methylation substrate is very slow. As described in phosphorylation and lysine acetylation study, the affinity enrichment is a key step in the global analysis which studies the protein post-translational modification (PTM) (Kim, S. C. et al. Substrate and functional diversity of lysine acetylation revealed by a proteomics survey. Mol Cell 23, 607-618 (2006)). Because the difference of physicochemical properties between the monomethylation modified lysine and the unmodified lysine, it is very difficult to separate the methylation modified lysine polypeptide by using chemical methods such as the Immobilized Metal Affinity Chromatography (IMAC) for separating the phosphorylated polypeptide (Ficarro, S. B. et al. Phosphoproteome analysis by mass spectrometry and its application to *Saccharomyces cerevisiae*. Nature biotechnology 20, 301-305 (2002)). In addition, it is also very difficult to prepare highly specific and high affinity anti-lysine monomethylated antibody. Therefore, it is required to innovate the existing technology basin on proteomics so as to identify and analyze the lysine methylation modification. Particularly, it is required to make completely new invention and innovation to the substrate identification and quantitative analysis method for lysine monomethylation modification.

SUMMARY OF THE INVENTION

The present invention relates to artificially synthesized modified monomethylated lysine, and modified monomethylated lysine derivatized polypeptide. The antibody produced by using the modified monomethylated lysine and modified monomethylated lysine derivatization polypeptide as antigen may be used in identifying and enriching the modified polypeptide lysine after in vitro derivatization of the monomethylated polypeptide, thereby playing a role in detecting the lysine monomethylation modified polypeptide and modified substrate.

In one aspect, the present invention provides a modified monomethylated lysine, said modified monomethylated lysine having the following structural formula:

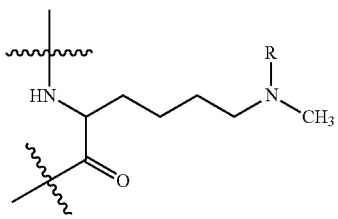

In some preferred embodiments where R is a modifying group, R may be

1) R is

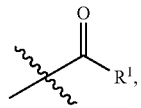

where $R^1$ is alkyl group (the carbon number of the modifying group is less than 6) or aryl group (the carbon number of the modifying group is less than 8); or 2) R is sulfonyl

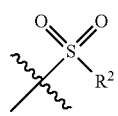

where $R^2$ is alkyl group (the carbon number of the modifying group is less than 6) or aryl group (the carbon number of the modifying group is less than 8). Preferably, R is

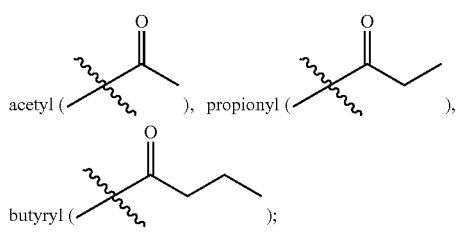

acetyl ( ), propionyl ( ), butyryl ( );

more preferably, R is

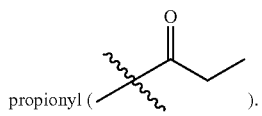 [SMILES: *C(=O)CC]

propionyl ( ).

On the other hand, the present invention also provides a modified monomethylated lysine derivatized polypeptide. The sequence of said modified monomethylated lysine derivatized polypeptide is CXnGGK*GGXn (SEQ ID NO: 1), where X is any amino acid among 19 types of common amino acids except for cysteine, n is 1-20; where the structure of K* is as follow:

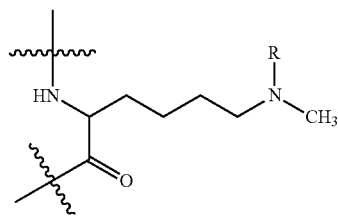

In some preferred embodiments where R is the modifying group, R maybe
1) R is

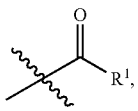

where R¹ is alkyl group (the carbon number of the modifying group is less than 6) or aryl group (the carbon number of the modifying group is less than 8); or
2) R is sulfonyl

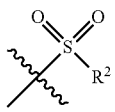

where R² is alkyl group (the carbon number of the modifying group is less than 6) or aryl group (the carbon number of the modifying group is less than 8). Preferably, R is

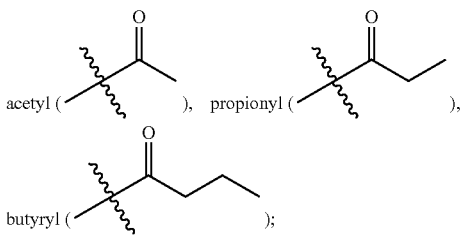

more preferably, R is

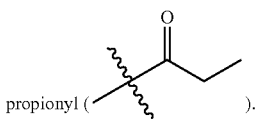

Preferably, the sequence of the polypeptide is CEGRGDSGGGK*GGSG (SEQ ID NO:2), where K* is selected from methyl propionylation, methyl acetylation or methyl butyryl modified lysines, in some preferred examples, K* is methyl propionylated lysine.

In a further aspect, the present invention provides an antigen. The antigen is formed by coupling the above-described modified monomethylated lysine or modified monomethylated lysine derivatization polypeptide with a carrier protein containing an activated group, said carrier protein includes but not limited to hemocyanin (KLH), bovine hemoglobin, bovine serumprotein (BSA) or ovalbumin (OVA) etc.

Preferably, the modified monomethylated lysine coupled with the carrier protein activated group is propionylated monomethylated lysine.

Preferably, the modified monomethylated lysine derivatized polypeptide coupled with the carrier protein activated group is monomethyl propionylated lysine polypeptide, the sequence of the polypeptide is CXnGGK*GGXn (SEQ ID NO:1), where X is any amino acid among 19 types of common amino acids except for cysteine, n is 1-20; K* is monomethyl propionylated lysine. Preferably, the polypeptide sequence is CEGRGDSGGGK*GGSG (SEQ ID NO:2), where K* is methyl propionylated lysine.

In a further aspect, the present invention provides an antibody. The antibody is prepared by immunizing an animal with the above-described antigen. The polyclonal antibody can be prepared by immunizing rabbits with an antigen which is the modified monomethylated lysine coupled with the carrier protein activated group; preferably, the polyclonal antibody can be obtained by immunizing rabbits with an antigen which is monomethyl propionylated lysine coupled with the carrier protein activated group.

The monoclonal antibody can be prepared by immunizing a mouse with an antigen which is a modified monomethylated lysine derivatizated polypeptide coupled with the carrier protein activated group. The sequence of the polypeptide coupled with the activated group of the carrier protein is CXnGGK*GGXn (SEQ ID NO: 1), where X is any amino acid among 19 types of common amino acids except for cysteine, n is 1 to 20, it is the number of the amino acid residues; K* is monomethyl propionylated lysine. Preferably, the sequence of the polypeptide coupled with the carrier protein activated group is CEGRGDSGGGK*GGSG (SEQ ID NO:2), where K* is methylpropionylated lysine.

The antibody provided by the present invention is able to specifically bond one polypeptide, this polypeptide includes one or more modified monomethylated lysines, its structure is as follow:

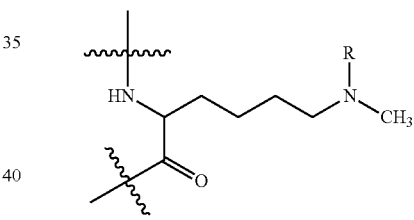

In some preferred embodiments where R is the modifying group, 1) R is

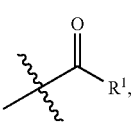

where R¹ is alkyl group (the carbon number of the modifying group is less than 6) or aryl group (the carbon number of the modifying group is less than 8); or 2) R is

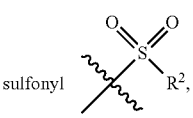

where R² is alkyl group (the carbon number of the modifying group is less than 6) or aryl group (the carbon number of the modifying group is less than 8). Preferably, R is

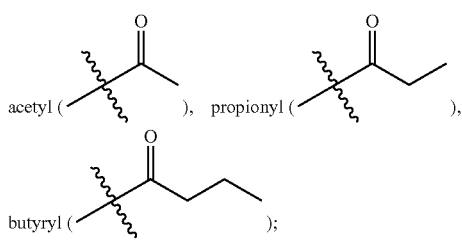

more preferably, R is

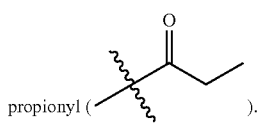

In addition to obtaining the antibody having above-described characteristics by immunizing animals, according to the theory of antibody development, the antibody can also be the modified monomethylated lysine or modified monomethylated lysine derivatizated polypeptide which is screened and prepared from bacteriophage display library, yeast display library, bacteria display library and ribosome display library. Preferably, the modified monomethyled lysine is monomethyl propionylated lysine, the sequence of the modified monomethylated lysine derivatizated polypeptide is CXnGGK*GGXn (SEQ ID NO: 1), where X is any amino acid among 19 types of common amino acids except for cysteine, n is 1-20, and it is the number of the amino acid residues; K* is monomethyl propionylated lysine. Preferably, the sequence of this polypeptide is CEGRGDSGGGK*GGSG (SEQ ID NO:2), where K* is methylpropionylated lysine.

According to another aspect, the present invention provides a method for identifying the monomethylation modification on a ε-amino group of lysine in a substrate peptide or protein, the method includes: using a in vitro nitrogen acylation derivatization reaction, derivatizing the lysine residues of monomethylated ε-amino group on said substrate into an acylation methylated ε-amino group; affinity enriching the peptide undergone the acylation methylation modification by an anti-acylation methylated pan antibody; identifying the presence of propionyl methylation modification in the antibody affinity enriched polypeptide by LC-MS.

Preferably, according to the results of liquid chromatography-mass spectrometry detection, and thereby determine or deduce the presence of the lysine monomethylation modification on the substrate protein or peptide.

Preferably, the total carbon number of the modifying group for nitrogen acylation modification to the substrate protein lysine residue monomethylated ε-amino group is less than 8. Preferred total carbon number is less than 6. Preferably, this modifying group can include alkyl or aryl, where the total carbon number of the alkyl or aryl is less than 8. Preferably, the total carbon number of the alkyl is less than 6, or, the total carbon atom number of the aryl is less than 8.

Preferably, the amino group of the lysine residues is derivatized to ethoxylated methylated ε-amino group, butyryl methylated ε-amino group, isobutyryl methylated ε-amino group, valeryl methylated ε-amino group, 2-methylbutyryl methylated ε-amino group, 3-methyl butyryl methylated ε-amino group, 2,2-dimethylpropionylation ε-amino group, succinyl methylated ε-amino group or malonyl methylated ε-amino group etc. The acylating reagent includes various carboxylic acids, anhydrides, acyl chlorides, and other all acylating reagents.

Preferably, the acylating reagent is an acylating reagent having stable isotope. The isotope acylating reagent are carboxylic acid, anhydrides, acyl chloride, carboxylic acid ester, amide and other all acylating reagents which contains carbon, hydrogen, oxygen, nitrogen stable isotope. Preferably, the stable isotope reagent is $^{12}C_6H_{10}O_3$ propionic anhydride, $^{13}C_6H_{10}O_3$ propionic anhydride or $^{12}C_6D_{10}O_3$ propionic anhydride.

In some other preferred embodiments, the substrate proteins or peptides are undergone in vitro nitrogen acylation reaction. In some preferred embodiments, acylation reaction of the substrate protein or peptide can be conducted before or after digestion of substrate by protease. Preferably, substrate protein or polypeptide is extracted from any cell, tissue or body fluid. Said substrate protein or polypeptide is total protein or total polypeptide.

In some preferred embodiments, the total protein extracted from cells or tissues are reacted with propionyl anhydride in a pH=8.5 ammonium carbonate-sodium bicarbonate buffer to afford in vitro lysine propionylate derivatized protein, after completion of the reaction, trypsin digested to produce lysine propionylation derivatized enzymolyzed polypeptide. In some preferred embodiments, preparation method of in vitro propionylated lysine derivatized protein include: 200 μL propionic anhydride is quickly added to a cell lysate containing 20 mg total protein, shaken and an appropriate amount of 2 M NaOH is added to adjust pH to 8, then incubated at room temperature for 30 minutes; after reaction the in vitro lysine propionylation derivatized protein is precipitated by trichloroacetic acid (TCA) precipitation method. To further produce the lysine propionylated derivatized enzymolyzed polypeptide, the precipitated protein was re-suspended in 2 ml of digestion buffer (0.1M NH4HCO3, pH=8.5), then the protein was digested by trypsin dissolved in a digestion buffer for 16 hours; after completion of the digestion, the precipitate is removed by centrifugation at 20,000×g for 10 minutes, to obtain a lysine propionylation derivatized enzymolyzed polypeptide supernatant. In a preferred embodiment, the ratio of trypsin to in vitro lysine propionylation derivatized protein is 1:100 (w/w).

In the in vitro lysine derivatization reaction, the ε-amino group of the modified lysine or monomethylation modification lysine are all undergone propionylation reaction, to produce propionylated lysine or propionyl methylated lysine, but dimethylated and trimethylated lysine do no undergo the above-described reaction. In theory, if propionylation reaction is complete, there is no unmodified lysine on the lysine residues of the protein after reaction. Therefore, after the protein reacted is enzymolyzed to produce enzymolyzed polypeptide, the polypeptide without any modification on the lysine residues are identified by mass spectrum analysis, the reaction efficiency of the propionylation reaction may be evaluated by comparing the ratio of this type of polypeptide in all identified lysine residues modified polypeptides.

In some preferred embodiments, before propionylation reaction said protein (total protein or total polypeptide, or specific protein or polypeptide) are extracted from the tumor cells or clinical sample cultured cells in culture medium. Preferably, the cells are the immortalized tumor cells based on cell cultured stable isotope labelling (SILAC). More preferably, in order to identify lysine monomethylated modified substrate in the cells, cells may be cultured in SILAC culture medium in which stable isotope amino acid was added. Preferably, the isotope amino acid includes $^{12}C$-arginine or $^{13}C$-arginine, more preferably, $^{12}C$-lysine or $^{13}C$-lysine, more preferably, the stable isotope amino acid is $^{12}CH_3$-methionine or $^{13}CD_3$-methionine. In some preferred embodiments, in order to provide methyl source in vitro for lysine methylation modification, to the cell culture medium $^{12}CH_3$-methionine ($^{12}CH_3$-Met) is added; or, to the culture medium $^{13}CD_3$-methionine ($^{13}CD_3$-Met) is added. Here, the $^{12}C$ of the methyl group on methionine is substituted by stable isotope $^{13}C$, $H_3$ (hydrogen) is substituted by stable isotope $D_3$ (deuterium).

During quantitative comparison of change of methylation modification in a pair of cells, it is needed to culture a cell in $^{12}CH_3$-methionine containing culture medium, and culture another cell in a stable isotope labeled $^{13}CD_3$-methionine containing culture medium, this method is known as amino acid stable isotope labelling strategy based on cell culture (SILAC) (Ong S E and Mann M. A practical recipe for stable isotope labelling by amino acids in cell culture (SILAC). Nat Protoc. 1(6): 2650-60. (2006)).

In some preferred embodiments, said cells are from commercially purchased cell lines, selected from one or more of K562 cells (chronic myeloid leukemia cell lines), SW620 cells (Colon cancer cell lines), A549 cells (non-small cell lung cancer cell line) and SMM7721 cells (liver cancer cells). The origin of the tissue is from excised liver cancer tissue sample of liver cancer patient.

In some preferred embodiments, it is required to conduct affinity enrichment of the specific anti-nitrogen acylated methylation pan antibody for nitrogen acylation methylation modified peptide. In preferred embodiments, the nitrogen acylated methylated lysine pan antibodies are coupled to the matrix which do not destroy the antibody affinity by chemical crosslinking, and the covalent bonding or non-covalent bonding. Said matrix is agarose resin, it is coupled to the agarose resin of protein A or protein G or protein A/G by non-covalent bonding; more preferably, non-covalent bonded to protein A agarose resin to prepare antibody-coupled resin.

Preferably, said pan antibodies are coupled to the matrix which do not destroy the antibody affinity by chemical crosslinking, covalent bonding or non-covalent bonding. Preferably, said pan antibodies are coupled to agarose resin of protein A or protein G or protein A/G by non-covalent bonding. More preferably, coupled to the protein A agarose resin by non-covalent bonding to prepare the antibody coupled resin.

In some preferred embodiments, said antibody are pan antibodies specifically bonded with propionyl methylated lysine. In some preferred embodiments, the used antibody is correspondingly detected by using the antibody of the present invention. This enrichment method includes the steps as follow: coupling the propionyl methylation pan antibody with the protein A coupled agarose resin, to prepare a protein A antibody coupled resin. In some embodiments, affinity enrichment also includes at incubating the propionyl methylation pan antibody with the lysine propionylation derivatized polypeptide at 4° C. overnight. Or incubating overnight using antibody coupled resin and the lysine propionylated derivatized polypeptide, then the antibody coupled resin after incubation was washed using 1 ml of NETN buffer (100 mM NaCl, 1 mM EDTA, 20 mM Tris pH 8.0 and 0.5% (w/v) NP-40); then the propionyl methylation modified peptide affinity enriched on the antibody resin is eluted with 100 μl of 0.1% (v/v) trifluoroacetic acid (TFA) for 3 times; the diluents are combined then drawn dry by a concentrator.

In some preferred embodiments, before the modified peptide is identified by liquid chromatography-mass spectrometry, HPLC separation is conducted to the enzymolyzed peptide of the protein after propionylation derivatization reaction, and affinity enrichment are conducted respectively to the propionyl methylation pan antibody for lysine propionylated derivatized polypeptide component after separation. Preferably, ionization treatment is conducted to the enriched polypeptide then Nano-HPLC/MS/MS mass spectrum analysis. By specific mass spectrometry data analysis software (Mascot or Maxquant) analysis, and mass displacement is identified corresponding to specific propionyl methylation modification on the lysine residues, and thereby confirm the monomethylation modification site on the polypeptide lysine residues modification, and modification polypeptide sequence and polypeptide sequence corresponding protein are quantified. Finally, the results of lysine monomethylated modified substrate identification and characteristic site modification level quantitative change are obtained.

BENEFICIAL EFFECTS OF THE PRESENT INVENTION

The present invention provides an artificially synthesized modified monomethylated lysine and modified monomethylated lysine derivatized polypeptide, using this modified monomethylated lysine and modified monomethylated lysine derivatization polypeptide as antigen, a specific antibody may be prepared by immunizing the animal, this antibody may be used in identifying and enriching the modified polypeptide after the lysine monomethylated polypeptide is in vitro derivatized, serving as detection lysine monomethylated modified polypeptide and modification substrate. In addition, by the detection method of the present invention, the lysine monomethylation modification in the substrate protein can be identified accurately and specifically, and quantitatively analyzed. By the method of the present invention, we verified 460 monometylation sites in 403 proteins, the method has a very high precision, and obtain a maximum lysine monomethylome by far. A small part of these 460 monometylation sites have been reported by previous studies, conforming effectiveness of the method of the present invention. But most are previously unknown lysine monomethylation modification site, this greatly enrich the knowledge to lysine monomethylation modification. The lysine methylation analysis of the present invention indicates function of this modification in in-cell pathway, metabolic network and composite structure. Our results provide the functional study of the subsequent lysine monomethylated pathway with rich data resources.

Illustration of Cell Hybrid Strain Collection

Name of the Collection Center: China General Microbiological Culture Collection Center, its Collection Number is CGMCC NO. 9109 of PMT-001 cell line, Classification Name: mouse-derived hybridoma cell, Collection Address: 1 of 3, Beichen West Road, Chaoyang District, Beijing Institute of Microbiology of the Chinese Academy of Sciences.

methyl propionylated lysine small molecule compound; 4: KLH coupled methyl propionylated lysine small molecule compound; 5: lysine propionylated polypeptide library; 6: lysine propionylated GG polypeptide; 7: lysine methyl acetylated polypeptide library; 8: lysine methyl acetylated GG polypeptide; 9: lysine methylbutyryl polypeptide library; 10: lysine methylbutyryl GG polypeptide; 11: unmodified lysine polypeptide library; 12: unmodified lysine GG polypeptide; 13: KLH.

Figure 1:
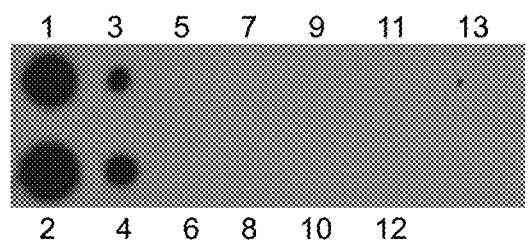
FIG. 1 shows a dot blot assay detection lysine methyl propionylation rabbit derived polyclonal antibody specificity. The loading amount corresponding to each of dot blot is 20 nanograms. 1: lysine methyl propionylated polypeptide library; 2: lysine methyl propionylated GG polypeptide; 3.
Figure 2:
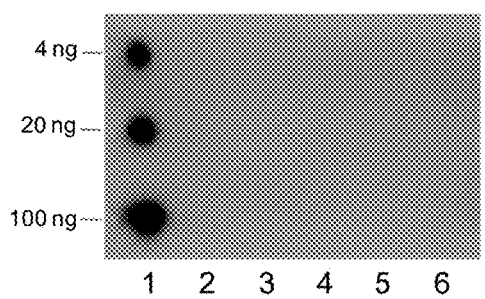

FIG. 2 shows a dot blot assay detection of specificity of lysine methylpropionylated rabbit derived polyclonal antibody. The corresponding loading amount of each dot blot is as shown on the left in the figure. 1: lysine methyl propionylated polypeptide library; 2: lysine propionylated polypeptide library; 3: lysine butyryl polypeptide library; 4: lysine monomethylated polypeptide library; 5: lysine di-methylated polypeptide library; 6: lysine trimethylated polypeptide library.

Figure 3:
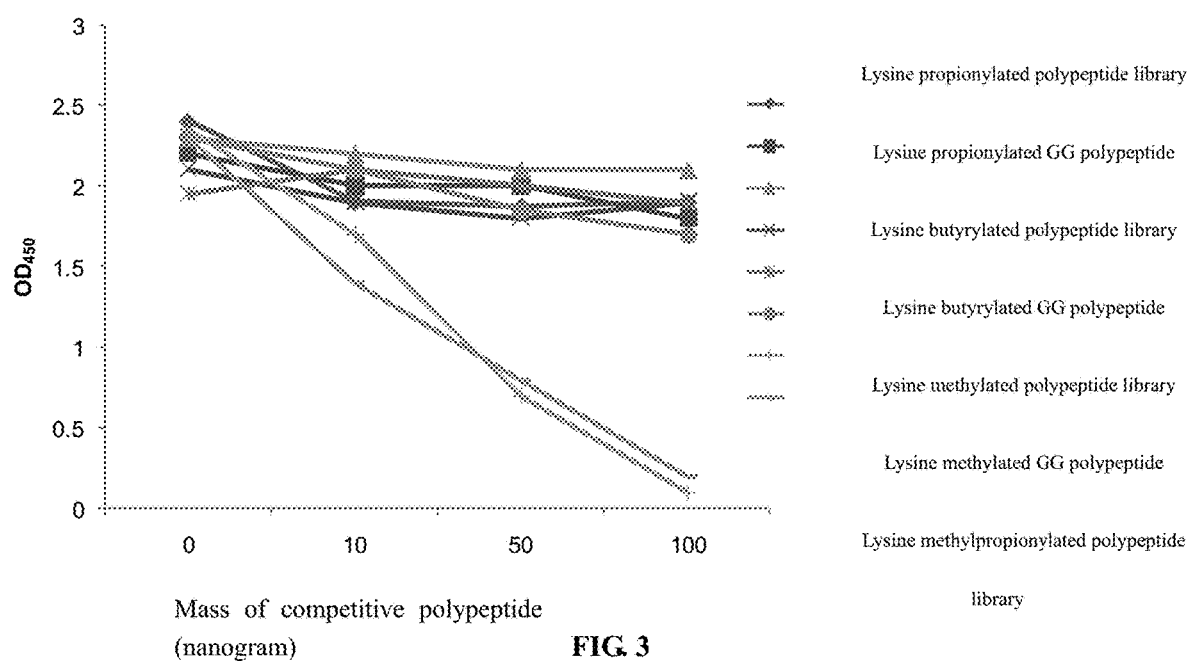

FIG. 3 shows specificity of the competition ELISA assay detection lysine methyl propionylated rabbit derived polyclonal antibody. The sequences of the polypeptides used in the experiments are seen in Table 1 and Table 2.

Figure 4:
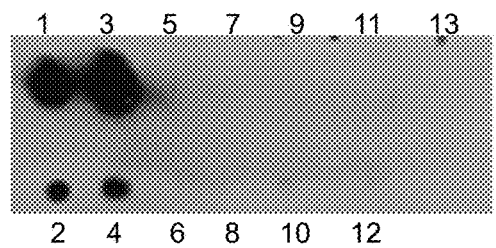

FIG. 4 shows dot blotassay detection of specificity of the lysine monomethyl propionylated mouse derived monoclonal antibody. The corresponding loading amount of each dot blot is 20 nanograms. 1: lysine methylpropionylated polypeptide library; 2: methyl propionylated lysine small molecule compound; 3: lysine methyl propionylated GG polypeptide; 4: KLH coupled methylpropionylated lysine small molecule compound; 5: lysine propionylated polypeptide library; 6: lysine propionylated GG polypeptide; 7: lysine methyl acetylated polypeptide library; 8: lysine methyl acetylated GG polypeptide; 9: lysine methylbutyryl polypeptide library; 10: lysine methylbutyrylated GG polypeptide; 11: unmodified lysine polypeptide library; 12: unmodified lysine GG polypeptide; 13: KLH. The sequences of the polypeptides used in the experiment are seen in Table 3 and Table 4.

Figure 5:
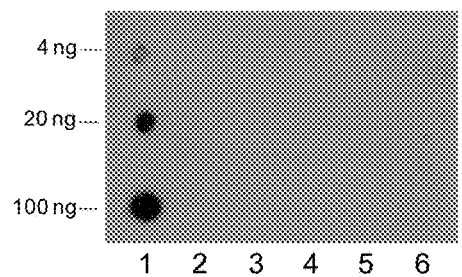

FIG. 5 shows a dot blot assay detection lysine monomethyl propionylated mouse-derived monoclonal antibody specificity. The corresponding loading amount of each dot blot is as shown on the left in the FIG. 1: lysine methyl propionylated polypeptide library; 2: lysine propionylated polypeptide library; 3: lysine butyryl polypeptide library; 4: lysine monomethylated polypeptide library; 5: lysine di-methylated polypeptide library; 6: lysine tri-methylated polypeptide library; the sequences of the polypeptides used in experiments are seen in Table 1 and Table 2.

Figure 6:
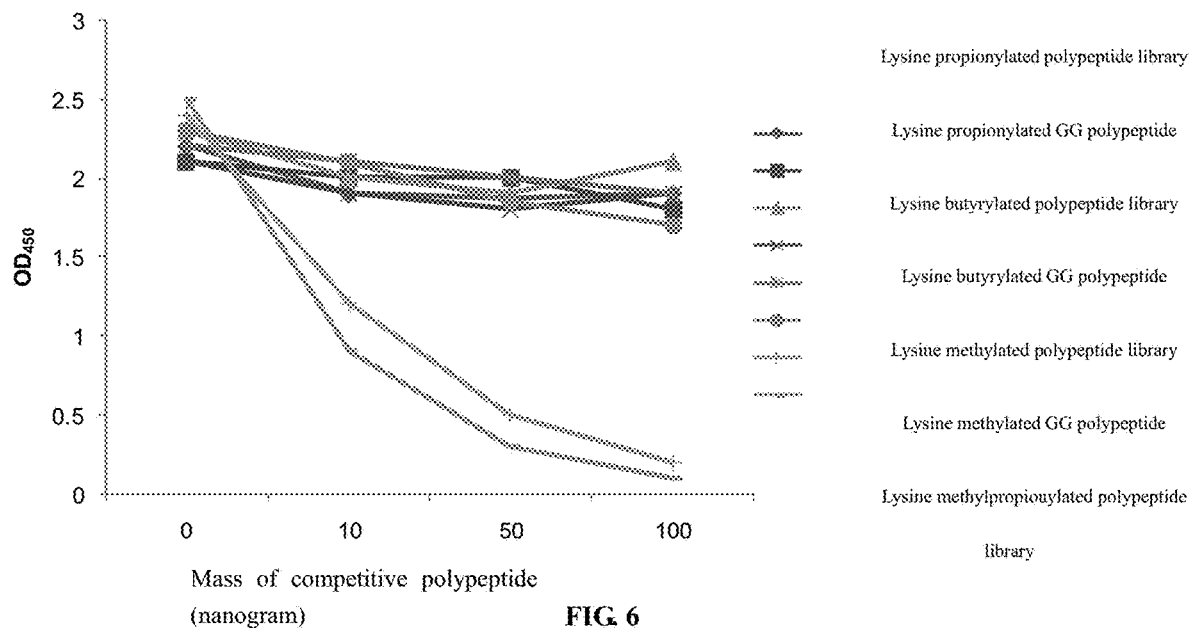

FIG. 6 shows competition ELISA assay detection lysine monomethyl propionylated mouse derived monoclonal antibody specificity. The sequences of the polypeptides used in the experiments are seen in Table 1 and Table 2.

Figure 7A:
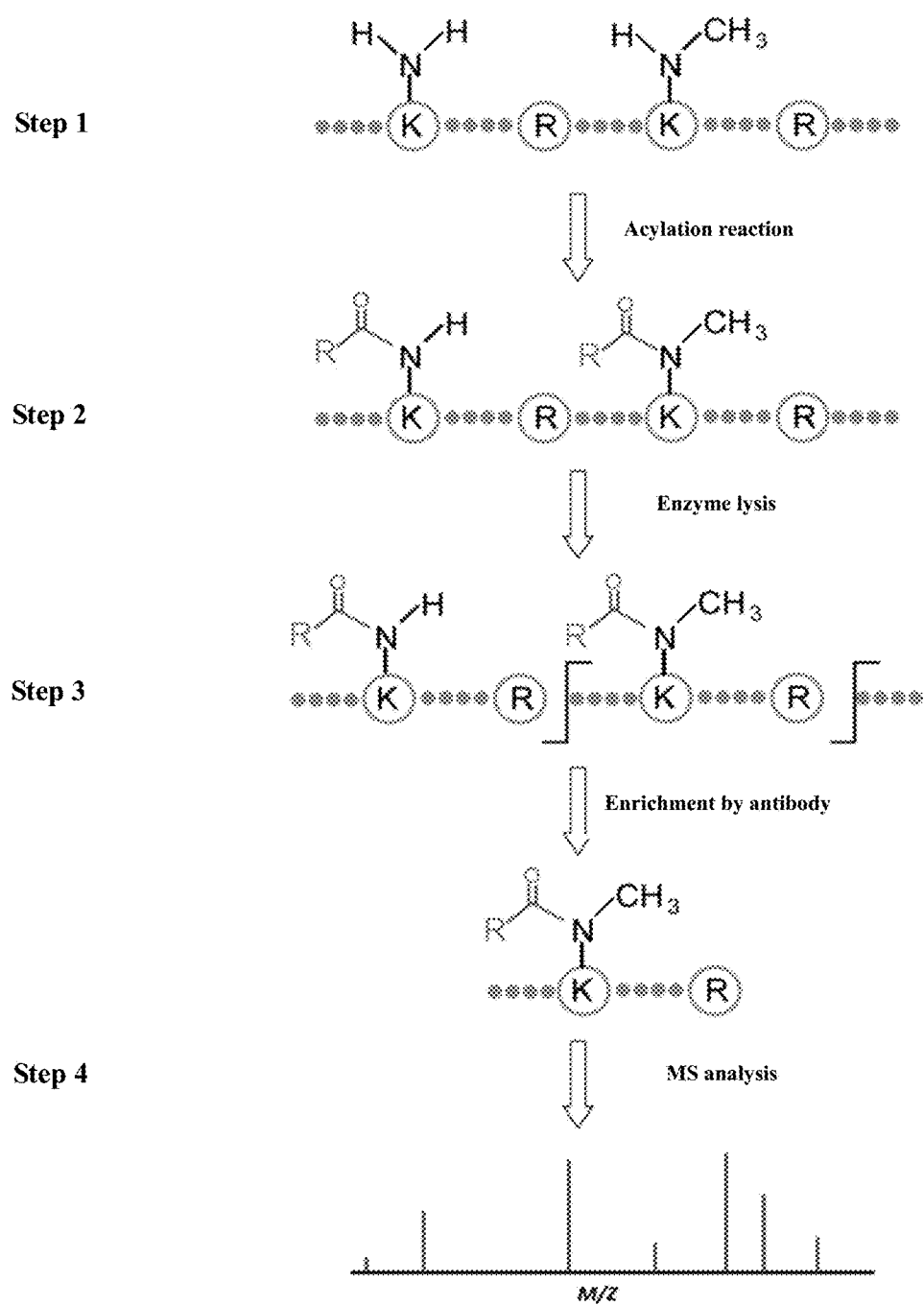
Figure 7B:
Figure 7B:
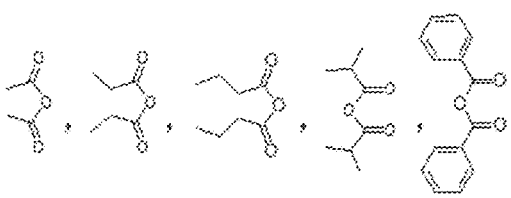
Figure 7B:
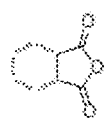
Figure 7B:
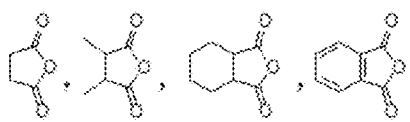
Figure 7B:
Figure 7B:
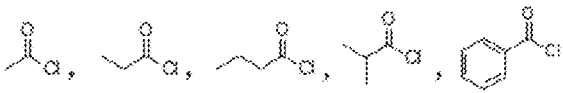
Figure 7B:
Figure 7B:
Figure 7C:
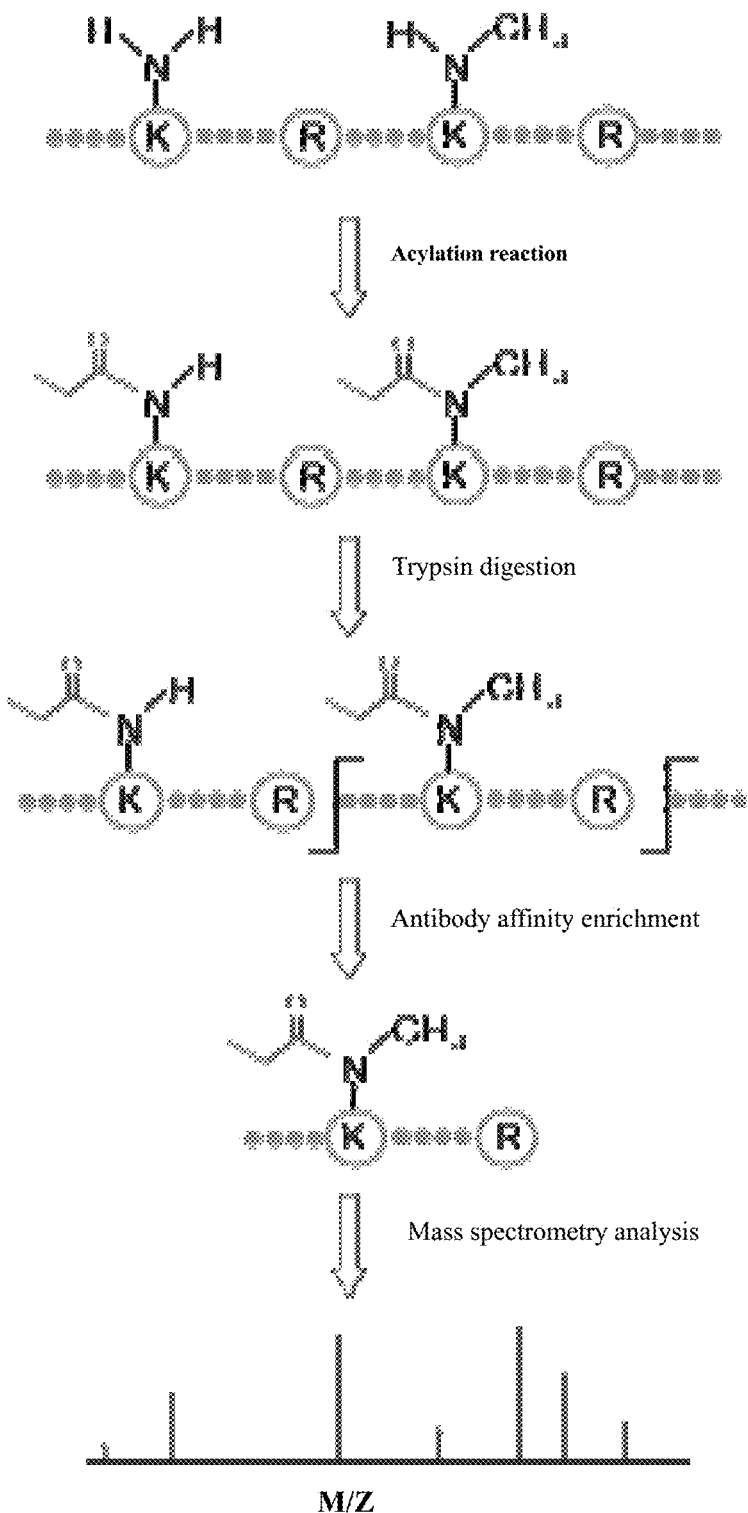
Figure 7D:
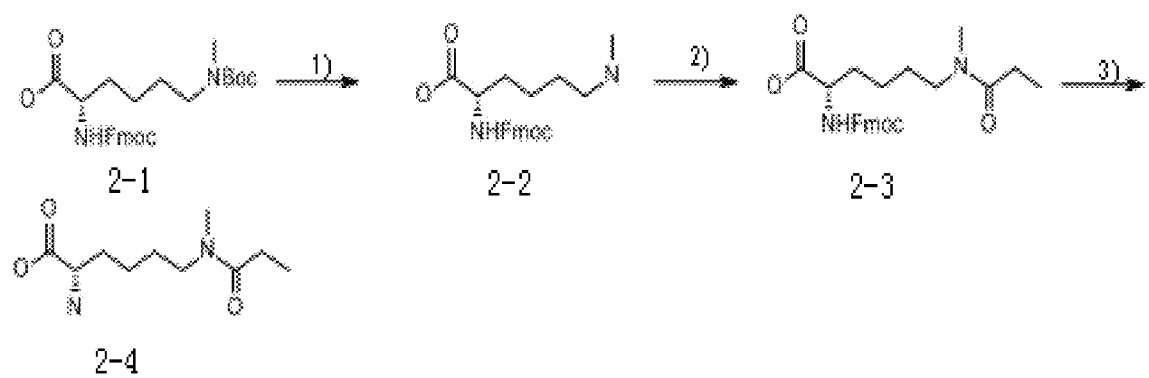
Figure 7E:
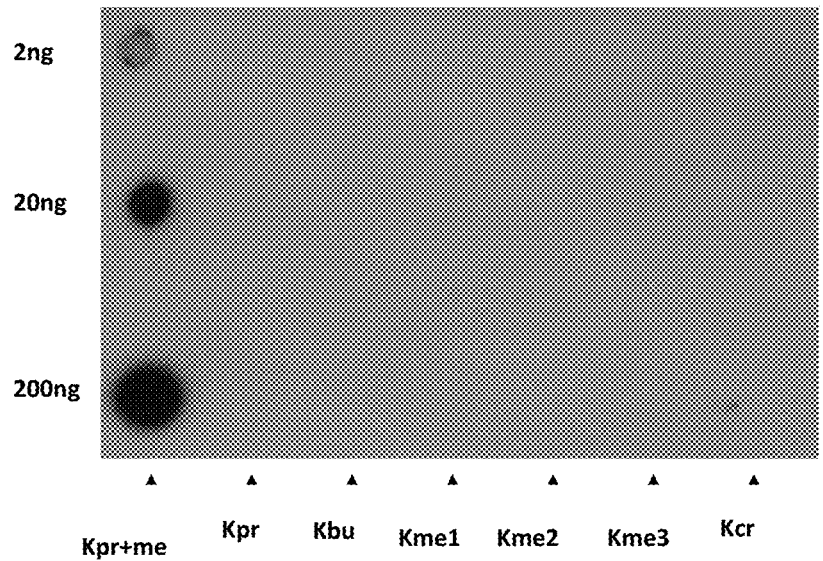
Figure 7F:
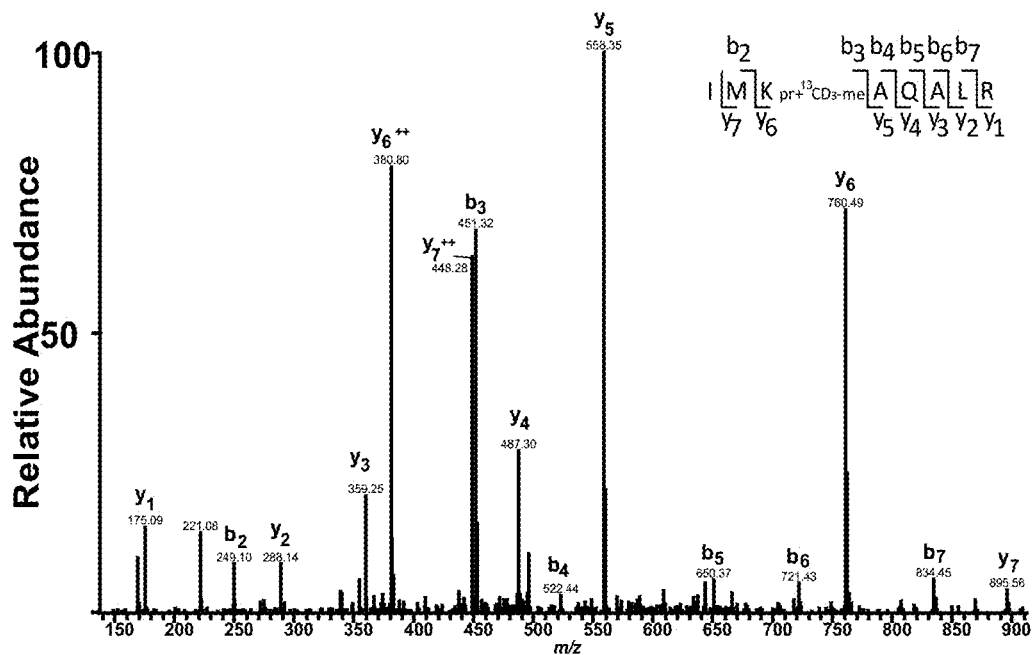

FIGS. 7A-7F are an assay design flowchart of the lysine monomethylated polypeptide identified in one specific example of the present invention. FIG. 7A is a flow schematic diagram of an assay identifying monomethylated polypeptide (lysine propionylation in vitro derivatization reaction, antibody affinity enrichment and mass spectrum analysis); FIG. 7B is common acylating reagent type; FIG. 7C is a flow schematic diagram of an assay identifying the monomethylated polypeptide which takes lysine propionylationin in vitro derivatization reaction, antibody affinity enrichment and mass spectrum analysis as example; FIG. 7D is a chemical synthesis scheme for producing propionyl monomethylated lysine of specific propionyl monomethylated lysine pan antibody. FIG. 7E is an assay of specificity of dot-spot detection propionyl monomethylated antibody, where $K_{pr+me}$ represents lysinepropionyl methylation polypeptide library, $K_{prop}$ represents lysine propionylated polypeptide library, $K_{bu}$ represents lysine butyryl polypeptide library, Kme represents lysine monomethylated polypeptide library, $K_{me2}$ represents lysine dimethylated polypeptide library, $K_{me3}$ represents lysine tri-methylated polypeptide library and $K_{cr}$ represents lysine butenoylated polypeptide library. FIG. 7F is an illustrative diagram of $MK_{pr+13CD3\text{-}me}$ AQALR typical mass spectrum analysis of one lysine propionyl methylated polypeptide of HSP90 protein. pr: propionylation, propionylation; me: methylation, methylation; pr+me: propionyl methylation, propionyl methylation; bu: butyrylation, butyryl; me2: di-methylation, dimethylation; me3: tri-methylation, trimethylation; cr: crotonylation, butenoylated.

Figure 8:
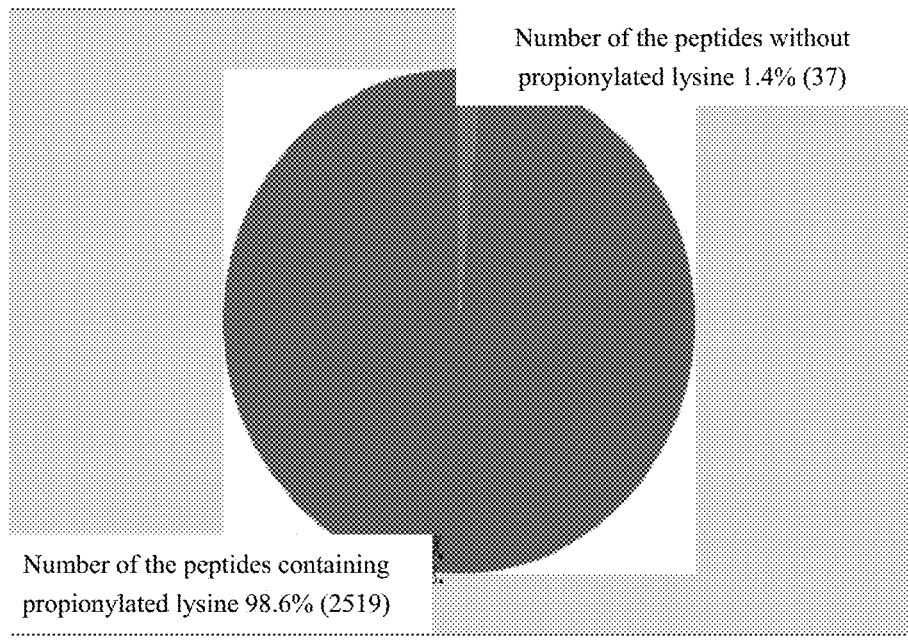

FIG. 8 is detection of lysine in vitro propionyl derivatization reaction efficiency. K562 cell total protein lysate after lysine in vitro propionyl derivatization reaction, obtain the enzymolyzed polypeptide bt trypsin digestion, mass spectrum analysis detection of the propionylated lysine in the enzymolyzed polypeptide. Lysine propionylation efficiency is evaluated by the ratio of propionylated lysine polypeptide in all identified polypeptides.

Figure 9A:
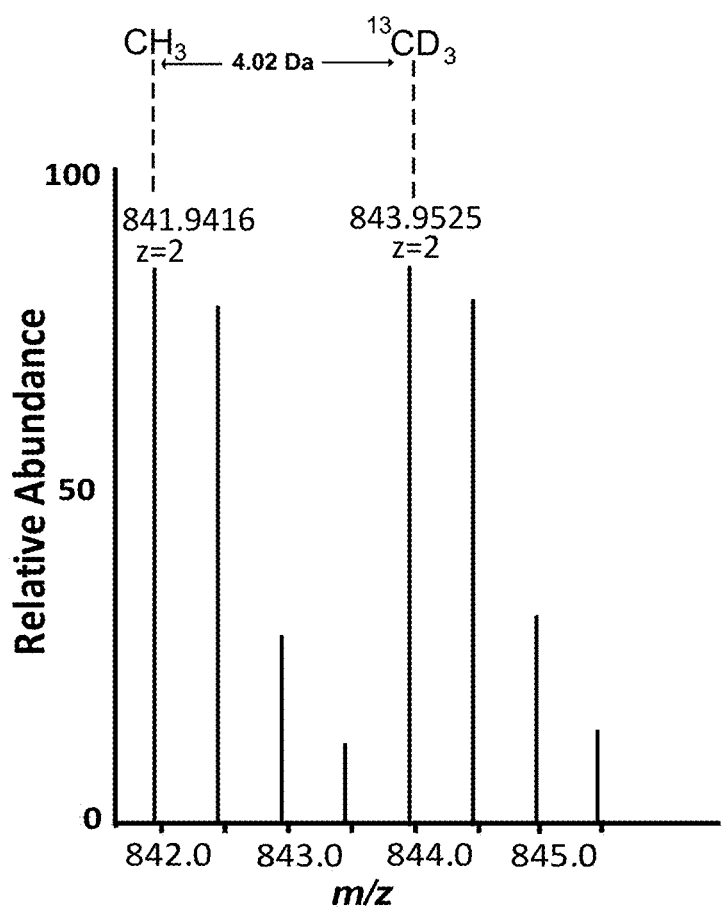
Figure 9B:
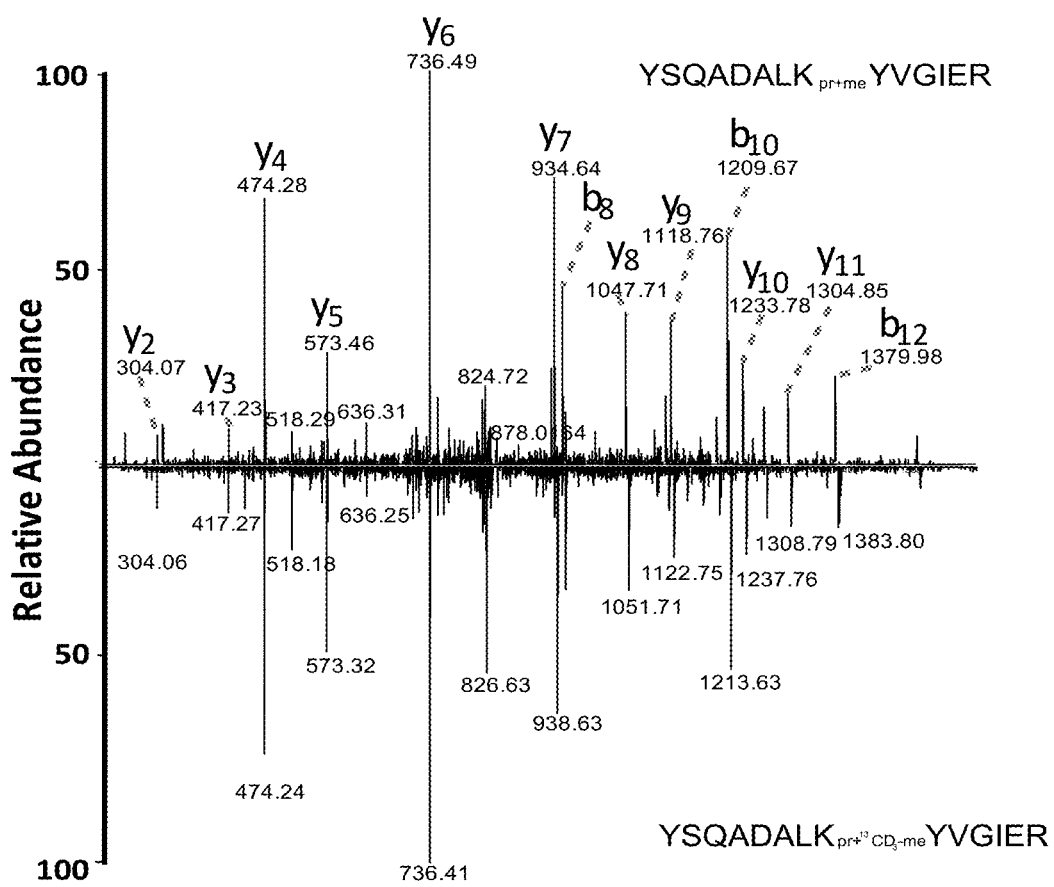
Figure 9C:
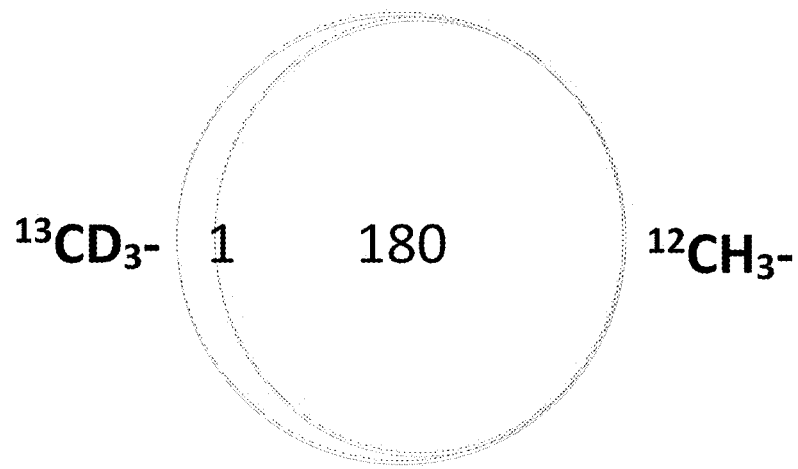
Figure 9D:
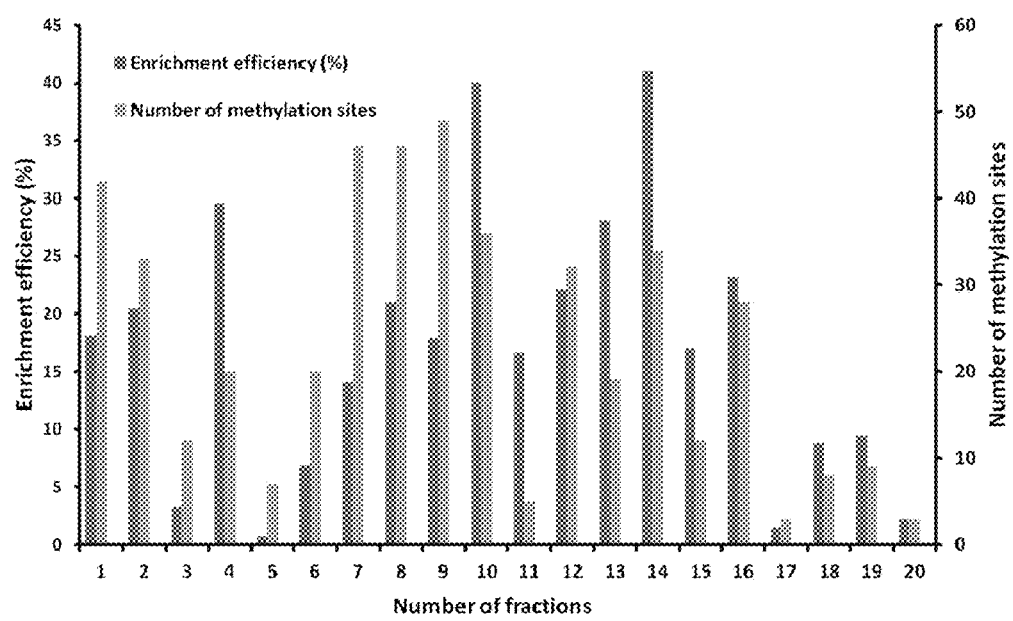

FIGS. 9A-9D are a characteristic spectrum of a lysine-propionyl methylation modification. FIG. 9A is MS spectrum of polypeptides after $^{13}CD_3$-Met labeled typical propionyl methylation modification. FIG. 9B is MS/MS mass spectrum of YSQADALK$_{pr+me}$YVGIER (SEQ ID NO:3) polypeptide of the EZH2 protein in HeLa cells. The upper part is $^{12}CH_3$-labeled YSQADALK$_{pr+me}$YVGIER (SEQ ID NO:3) peptide MS/MS mass spectrum, where, the lower part is a mass spectrum of $^{13}CD_3$-labeled YSQADALK$_{pr+}{}^{13}{}_{CD3\text{-}me}$VYGIER (SEQ ID NO:4) polypeptide, it shows a 4 Da mass transfer of b-, y-ion of the same propionyl methylation polypeptide after stable isotope labelling. FIG. 9C is a methylation polypeptide number comparison diagram identified from "light" ($^{12}CH_3$—) and "heavy" ($^{13}CD_3$-) methionine labeled HeLa cell lysate mixture. FIG. 9D shows number of the lysine monomethylated polypeptide and enrichment efficacy of antibody after 20 polypeptide components separated and obtained by basic HPLC column undergoes pan propionyl methylation antibody enrichment mass spectrometry identifies. pr: propionylation, propionylation; me: methylation, methylation; pr+me: propionyl methylation, propionyl methylation.

Figure 10A:
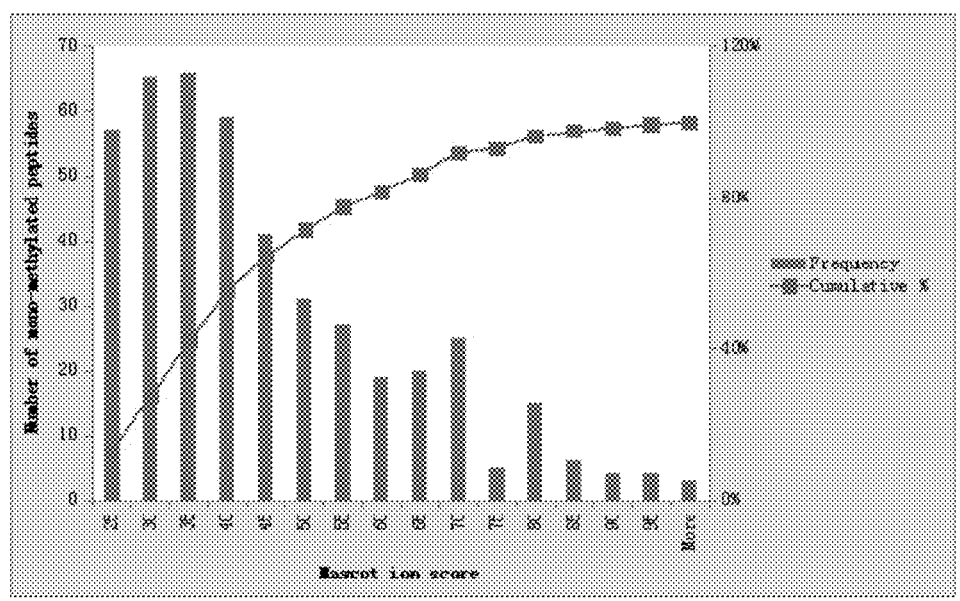
Figure 10B:
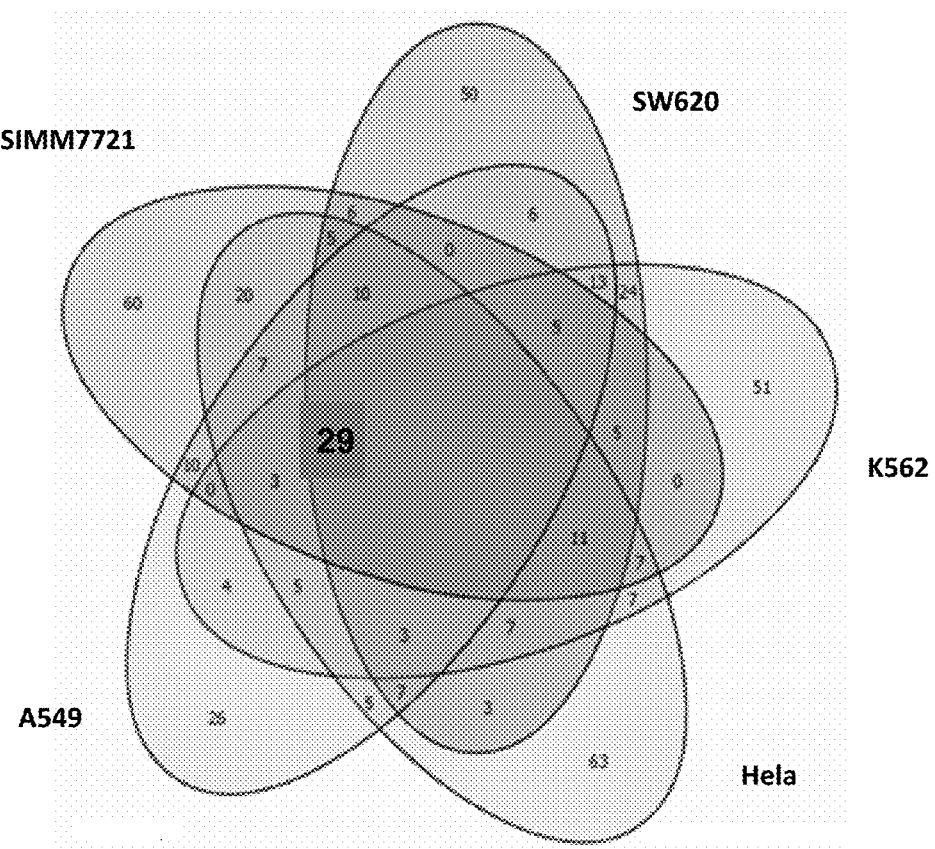

FIGS. 10A-10B are a protein lysine monomethylated group with high confidence. FIG. 10a is a distribution diagram of Mascot ion score of all 463 identified monomethylated polypeptides in all samples; it only shows the polypeptide with a Mascot ion score higher than 30. FIG. 10b is a Venn diagram of the number of the lysine monomethylated polypeptide identified from 5 tumor cell lines (HeLa (cervical cancer cells), K562 (chronic myeloid leukemia cells), SW620 (colon cancer cells), A549 (lung cancer cells) and SMM7721 (liver cancer cells).

Figure 11A:
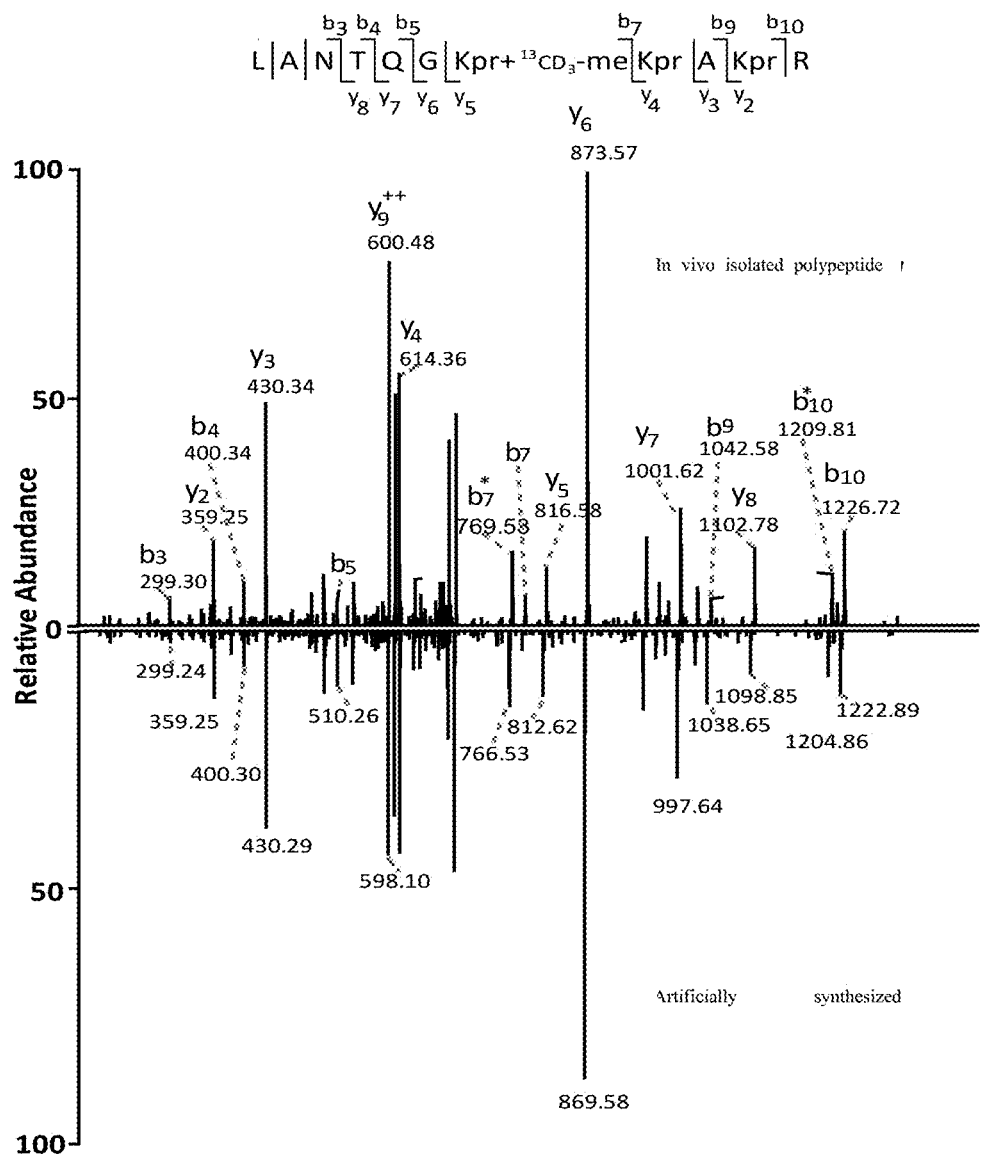
Figure 11B:
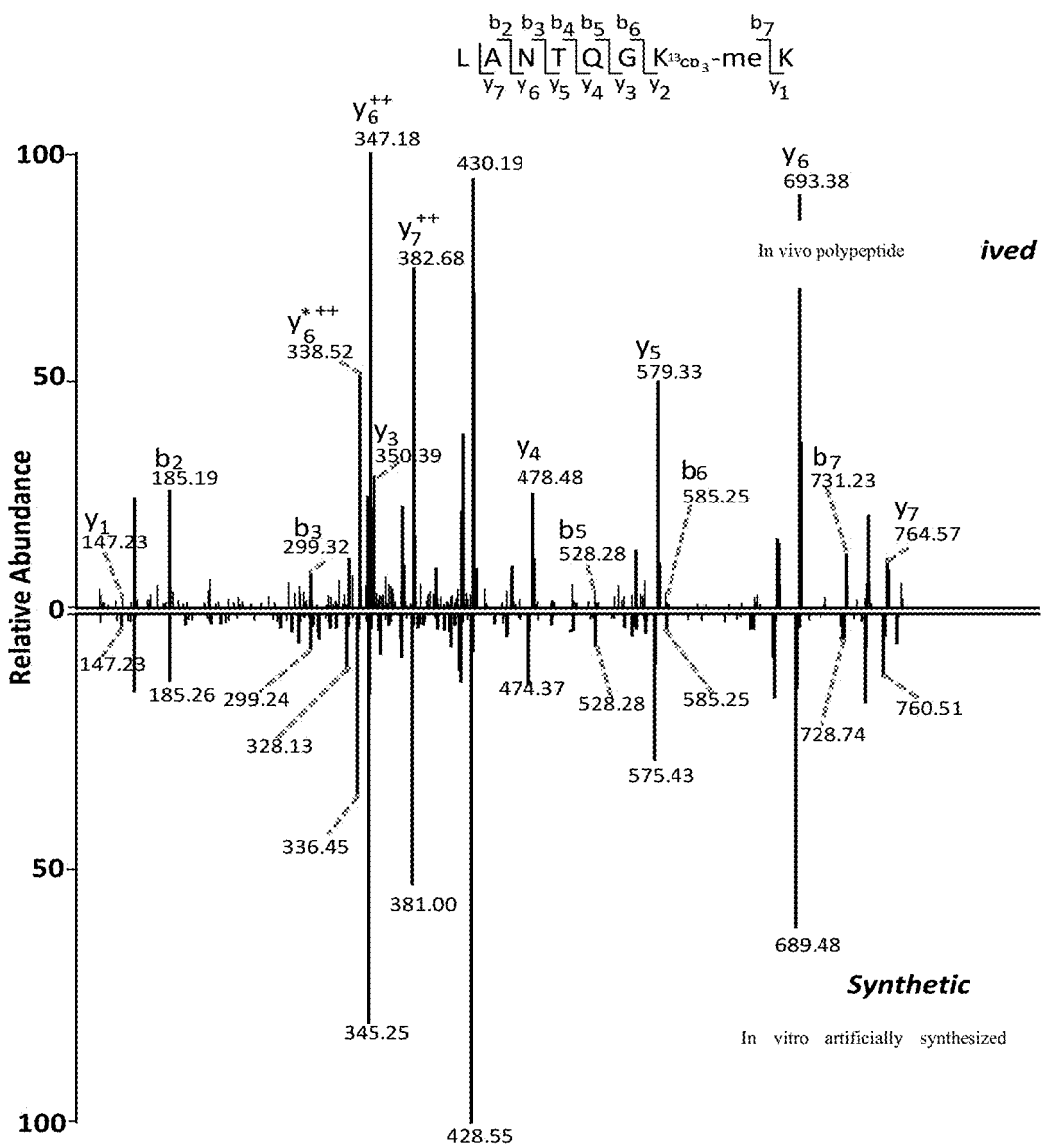

FIGS. 11A-11B are a verification diagram of the mass spectrometry of propionyl methylation site of CDC5L protein K114 in K562 cells. FIG. 11A is LANTQGK$_{pr+me^-}$K$_{pr}$AK$_{pr}$R (SEQ ID NO:5) tandem mass spectrum analysis of a synthesized propionyl methylation polypeptide, it shows same ionic strength as the polypeptide from K562 cells, the upper part of the diagram is a LANTQGK$_{pr+me}$K$_{pr}$AK$_{pr}$R (SEQ ID NO:5) mass spectrum of the polypeptide in vivo identified by the present invention, the lower part is mass spectrum of the synthetic polypeptide. FIG. 11B is a 4 Da transfer of y-ion and b-ion in tandem mass spectrum analysis of in vivo polypeptide LANTQGKmeK (SEQ ID NO:6) and its in vitro synthetic polypeptide LANTQGKmeK (SEQ ID NO:6), it is same as the location transfer of the lysine methyl residues. pr: propionylation, propionylation; me: methylation, methylation; pr+me: propionyl methylation, propionyl methylation.

Figure 12A:
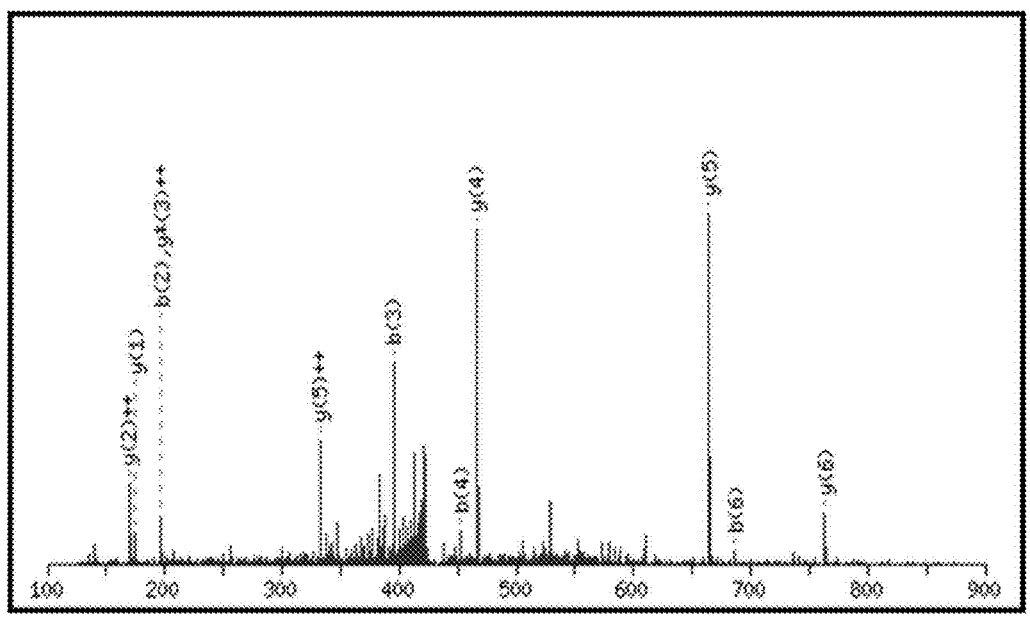
Figure 12B:
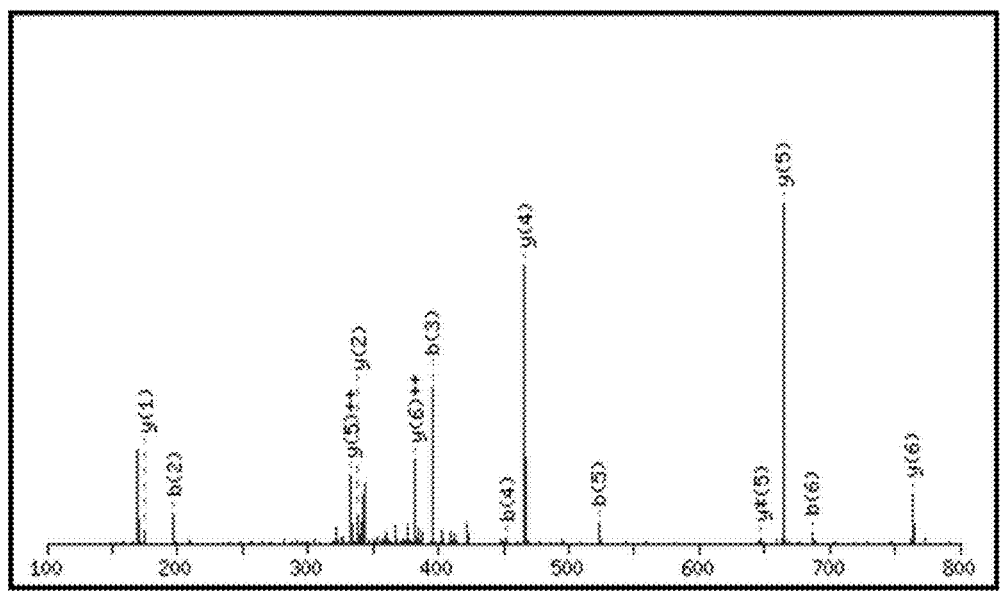
Figure 12:
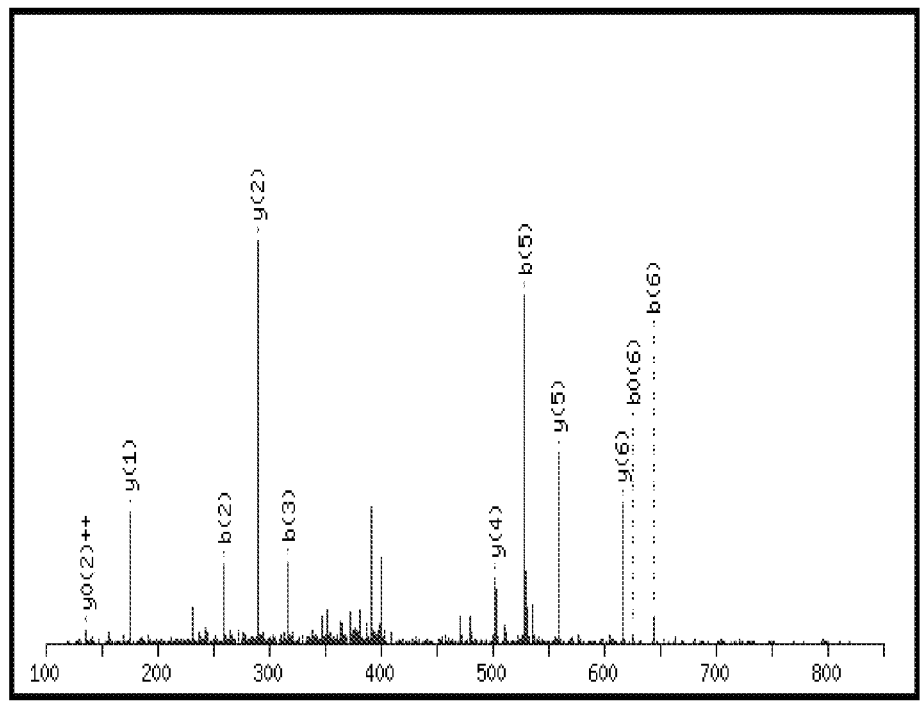
Figure 12D:
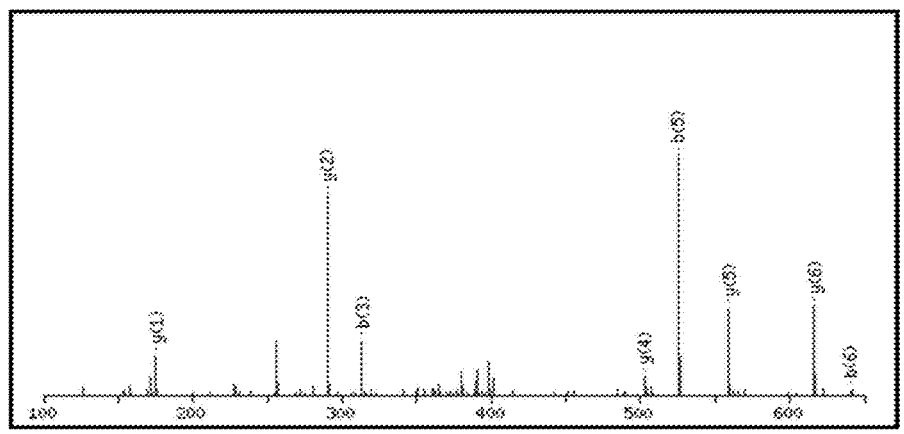

FIGS. 12A-12D are an illustrative diagram of mass spectrometry verification of lysine propionyl methylation polypeptide. The illustrative diagram of the mass spectrometry is from the comparison of in-cell lysine propionyl methylation polypeptide with corresponding synthetic polypeptide. Wherein, FIG. 12A is a secondary mass spectrometry (MS/MS) diagram of $PVK_{pr+me}GAYR$ (SEQ ID NO:7) peptide identified from KHDRSB1 protein in HeLa cells (where $K_{pr+me}$ represents propionyl monomethylated lysine). FIG. 12B is a mass spectrum ($PVK_{pr+me}GAYR$ (SEQ ID NO:7)) of corresponding in vitro synthetic polypeptide. FIG. 12C is a secondary mass spectrometry (MS/MS) of $K_{pr+me}GGPDDR$ (SEQ ID NO:8) peptide identified by K562 cell EIF4H protein (where $K_{pr+me}$ represents propionyl monomethylated lysine); FIG. 12D is a secondary mass spectrum ($K_{pr+me}GGPDDR$ (SEQ ID NO:8)) of the corresponding in vitro synthetic polypeptide. pr: propionylation, propionylation; me: methylation, methylation; pr+me: propionyl methylation, propionyl methylation.

FIG. 13 is a modification site diagram identified for different cells of the present invention; 29 lysine monomethylated modified protein are identified in five tumor cell lines (HeLa (cervical cancer cells), K562 (chronic myeloid leukemia cells), SW620 (Colon cancer cells), A549 (lung cancer cells) and SMM7721 (liver cancer cells).

DETAILED DESCRIPTION

Definitions

Unless otherwise defined, all technical and scientific terms use herein have the same meaning as the terms used by those skilled in the art of the present invention.

Modification of Lysine and Design of Antigen

In some preferred embodiments, on the basis of lysine monomethylation modification, acetyl, propionyl or butyryl modification can be conducted to the monomethylated lysine, then animals are immunized by small molecule compound or polypeptide antigen with dual modifications to obtain an antibody specifically identifying lysine monomethyl acetylation (Kme-ac), monomethyl propionylation (Kme-prop) or monomethyl butyryl (Kme-buty).

Usually, after trypsin lysis is conducted to a protein sample extracted from organism, an in vitro derivatization reaction such as propionylation reaction may be conducted to the enzymolyzed polypeptide. If lysine monomethylation modification is present in a certain polypeptide, a lysine monomethylated propionylated polypeptide will be obtained after in vitro derivatization. Then the lysine monomethylated propionylation after polypeptide derivatization reaction is conducted and above-described develop antibody are incubated, according to antigen-antibody specific affinity binding characteristics, lysine monomethylpropionylated antibody would specifically identify and enrich lysine monomethylated propionylated polypeptide. The lysine monomethylated propionylated polypeptide bonded with the antibody is eluted by acid elution, subsequently by mass spectrum analysis we can know information about polypeptide sequence of the lysine monomethyl propionylation modification and modification site, these information are actually corresponding to polypeptide sequence and modification site of lysine monomethylation modification, finally by further protein data searching we can obtain information about protein substrate of the lysine monomethylation modification.

Group modification to amino acid is a technology known by those skilled in the art. Such modification can be found in modification of natural organism for separation and purification, and manual in vitro modification can also be conducted to obtain modified amino acid. Lysine according to its nature, in vivo is easy to undergo various modification, such as acetylation lysine, methylation lysine etc. in vitro, under optimized reaction system and reaction condition, synthetic specific lysine modification, such as monomethyl acetylation lysine, monomethyl propionylated lysine monomethyl butyrylated lysine. Such artificially synthesized modified lysine small molecule, one aspect may be used as small molecule antigen and necessary carrier protein coupled to immunize animal to produce antiserum, by necessary antibody purification process, to produce antibody of specific identify this modified lysine. On the other hand, using the synthetic modified lysine as raw material, further artificially synthesized polypeptide antigen. Immunizing animal with the polypeptide antigen coupled with necessary carrier protein to produce antiserum, by necessary antibody purification process, as antibody specifically identifying this modified lysine.

The length of artificially synthesized modification lysine polypeptide antigen is within 30 amino acid residues of the modified lysine, the preferred sequence length is CXnGGK*GGXn (SEQ ID NO: 1), where X is any amino acid among 19 common amino acids except for cysteine, n is 1-20; K* is modified lysine, preferably, K* is selected from methyl propionylation, methyl acetylation or methyl butyryl modified lysine. In some preferred embodiments, K* is methylpropionylated lysine. In some preferred embodiment, the modified amino acid can be at middle position of the polypeptide sequence, is also can be in this polypeptide antigen amino end (—NH2) or carboxyl end (—COOH) position. Preferably, the sequence of the polypeptide antigen is CEGRGDSGGGK*GGSG (SEQ ID NO:2).

Synthesis of Antigen Polypeptide

The synthesis of the modified lysine polypeptide is a well-known technology. Solution method can be used to synthesize the polypeptide of the present invention, but common solid phase synthesis method can also be used to synthesize the polypeptide of the present invention. Chemical synthesis liquid phase method or solid phase method for polypeptide is mature. In some preferred embodiments, the technology for synthesizing the polypeptide is solid phase synthesis method. In 1978, Chang Meienlofer and Atherton et al. using the Fmoc (9-fluorenylmethoxycarbonyl) reported by Carpino as the protecting group of α-amino group, Fmoc group is very stable to acid, but it can be removed by piperidine-CH$_2$CL$_2$ or piperidine-DMF. In recent years, Fmoc synthesis method was widely used. In some other preferred embodiments, the Fmoc synthesis method is used to synthesize the peptide chain sequence of the present invention (Fmoc Solid Phase Peptide Synthesis)—A Practical Approach. Oxford University Express, 2000).

The basic method for synthesizing the peptide chain sequence by Fmoc synthesis method of the present invention is: firstly α-amino group protected amino acid one arm by one Fmoc group is linked to one insoluble carrier, then the α-amino group is deprotected, with an elution wash amino acid-arm-resin. Then, second pre-activated α-amino group protected amino acid was linked by coupling reaction. Moreover, the coupling reaction may also be conducted using α-N end and side-chain protected peptide fragment in placement of single amino acid, after completion of the condensation reaction, washed with a solution, deprotection was repeated, coupled, until the target peptide was obtained. Finally, peptide-arm-resin is lysed. Such solid phase synthesis method for lengthening peptide chain may be in continuous method, but also continuous flow method.

Antibody and Production of Antibody

Here, antibody refers to an antibody obtained by immunizing animals using the modified lysines mall molecule or modified lysinepolypeptide of the present invention as antigen.

In some preferred embodiments, in case of carbodiimide, such as 1-(3-dimethylaminopropyl)-3-ethylcarbodiimidehydrochloric acid salt (EDC) is present, carboxylic end (—COOH) of the modified lysine small molecule can reacted with N-hydroxysuccinimide sulfonic acid (Sulfo-NHS), to give semi-stable Sulfo-NHS ester, then coupled with amino end (—NH2) of the carrier protein (Taros, J. V., et al., Anal Biochem, 156:220-2(1986)). the present invention small molecule compound monomethyl propionylated lysine (Lys(me-prop)-OH), by EDC, some carrier protein —NH2 end coupling, forming an activated total antigen to immunize animals. In the preparation of polypeptide total antigen, amino group (—NH2) on the carrier protein first reacts with 4-(N-maleimide methyl) cyclohexane-1-carboxylic acid sulfonic acid succinimide ester sodium salt (sulfo-SMCC), forming a stable peptide bond, then reacted with cysteine at the terminal of antigen polypeptide, forming a stable complex by disulfide bond, thereby forming an activated total antigen for immunizing animal.

In some preferred embodiments, modified lysines mall molecule or antigen polypeptide of the present invention was activated by coupling with the carrier protein, modified lysine small molecule or polypeptide antigen with carrier protein has more potent immunoactivity, because individual modified lysine small molecule or polypeptide sequence its self usually has no immunoactivity or the immunoactivity is very low. The coupled carrier protein may be but not limited to Keyhole limpet hemocyanin (KLH), Bovine Serum Albumin (BSA), Ovalbumin (OVA), Bovine gamma globulin (BGG), Bovine Thyroglobulin (BTG), Sperm Whale Myoglobin (SWM), Tetanus Toxoid (TT), Methylated Bovine Serum Albumin (mBSA), Human immunoglobulins IgG IgA or other immunogen proteins of prior art etc.

Animals can be immunized using above modified lysines small molecule or polypeptide couple with active group, such as mouse, rabbit, or other mammals to produce multiclone antibody, but hybridoma cell can also be used to produce monoclonal antibody, these methods are well-known technologies in the art, here not described any more, can refer to some textbooks or immunization handbook to obtain the antibody or antibody fragment of the present invention (Making AND Using Antibodies-A practical handbook). CRC Press, 2007). Of course, the antibody can also be produced naturally, it may also be artificially synthesized antibody or antibody fragment. These antibodies can specifically identify the lysine residues including modified, not related with its surrounding sequences. In some preferred embodiments, the antibody of the present invention can specifically identify monomethyl propionylation modified lysinepolypeptide, but cannot identify the polypeptide having other lysine modifications. So-called "specificity" refers to antibody only can identify or bond a certain specific type of antigen, but not identify or bond other type of antigens. In the present invention, the prepared antibody can only identify peptide chain sequence of monomethylpropionylated modified lysine, but cannot identify polypeptide sequence of other type of lysine modification, including but not limited to lysine dimethylation, trimethylation, acetylation, propionylation, butyryl modification, or other modification of amino acid residues, such as tyrosine phosphorylation etc.

As bond or identify lysine methyl propionylation modification antibody, may be antibody of the present invention. The antibody maybe immunizing protein molecule or some antigen specific site immunoglobulin molecule, e.g., the molecules having antigen bonding site are able to specifically (immunized) bond analyzed material, pseudo material of the analyzed material or ligand. Antibody also includes artificially synthesized hybridized antibody or modified antibody or antibody molecule fragment, includes but not limited to antibody fragment and Fv fragment. The antibody having a function of bonding antigen have naturally occurring antibody some fragments. One bonded fragment or antibody fragment includes without limited to (i) Fab fragment, it includes L, VH, CL and CH1 region; (ii) Fd fragment, it includes VH and CH1 regions (iii) Fv fragment, it includes VL and VH regions one single chain of the antibody; (iv) dAb region (Ward et al., Nature 341:544-546 (1989), it includes VH region; (v) one independent epitope (CDR); (vi) one F(ab') 2 fragment, one divalent fragment includes two Fab fragment linked in hinge area by disulfide bond. In addition, while the two regions on this Fv fragment is determined by different gene encoding, the artificially synthesized reagent can form single protein chain (a known single Fv (scFv) chain) (Bird et al., Science 242:423-426 (1988); and Huston et al., PNAS 85:5879-5883 (1988)). The protein fragment includes the fragments may cross linked to their target antigens, e.g., divalent fragment, such as F (ab')2 fragment. Optionally, the protein fragment of those cannot be self-crosslinked target antigen may also bond to the target along with antigen secondary antibody.

Substrate Labelling of Lysine Monomethylation Modification

Methylation modification of amino acid is a naturally occurring phenomenon or procedure. Based on current study indicate, cell in vivo, S-adenosine-L methionine (SAM) is the most important direct donor of methyl group, and methionine (Met) is direct premise of synthesizing SAM. Therefore, when methionine was added into the culture medium, after a series of in vivo reaction pathway in cell, methyl group ($CH_3$—) on the methionine may be transferred to ε-amino group of lysine to obtain methylation modification. This constitutes general theory of lysine methylation modification substrate labelling, to the cell culture medium different stable isotope labeled methionine are added, such as $^{12}CH_3$-Met or $^{13}CD_3$-Met, respectively substrate protein carry $^{12}CH_3$-methyl group or $^{13}CD_3$-Met methyl group. The brief description of the labelling pathway is as follow:

A: $^{12}CH_3$— methionine→S-adenosine-L methionine-$^{12}CH_3$(SAM)→lysine-$^{12}CH_3$ (lysine monomethylated)

B: $^{13}CD_3$-methionine→S-adenosine-L methionine-$^{13}CD_3$ (SAM)-lysine-$^{13}CD_3$ (lysine monomethylated).

For one of lysinemono methylated modification of the same sequence polypeptide, the only difference between labelling by $^{12}CH_3$-Met or $^{13}CD_3$-Met is, because of difference in the molecular weight of the stable isotopes, this polypeptide labelled by $^{13}CD_3$-Met will be 4.02 Da heavier than the polypeptide of the same sequence labeled by $^{12}CH_3$-Met (FIG. 9a), to distinguish these two polypeptides by change of mass displacement by mass spectrum analysis, but the amount of polypeptide can be reflects by mass spectrum analysis of abundance. This constitutes same conditions protein modification quantify analysis, it is called as amino acids table isotope labelling strategy (SILAC) based on cell culture (Ong S E and Mann M. A practical recipe for stable isotope labelling by amino acids in cell culture (SILAC). Nat Protoc. 1 (6): 2650-60 (2006)). For qualitative analysis of lysine monomethylated modified substrate in cell or tissue, stable isotope labelling strategy, directly by antibody enrichment, the method of mass spectrum analysis can be realized. For quantifying the lysine monomethylation modification level a pair of genetic background cell sample, it is needed to introduce $^{12}CH_3$-Met or $^{13}CD_3$-Met labeled SILAC strategy, then by antibody enrichment, mass spectrum analysis method.

How to Determine or Quantify Certain Protein Modifications by Mass Spectrometry Technology, Include Lysine Methylation Modification, Technical Methods as Known by Those Skilled in the Art Propionylation Derivatization Reaction of Lysine Monomethylation Modification Under normal circumstances, identification of a certain protein modification substrate first to affinity enriching the modified polypeptide of modification specific pan antibody, such as identification of acetylated substrate. However, for lysine monomethylation modification, since the methyl group is too small ($CH_3$—) and the immunogenicity is very weak, it is difficult to directly obtain lysine monomethylated modified pan antibody. In order to overcome this difficulty, inventors van specificity lysine monomethylation modification lysine ε-amino by in vitro derivatization reaction to introduce additional groups, increasing the space structure of lysine ε-amino group modifying group, provide preparation of antibody with larger epitope and stronger immunogenicity.

Lysine propionylation reaction is an in vitro derivatization reaction known by those skilled in chemical reaction and synthesis, by reacting propionic anhydride with substrate protein under in vitro specific reaction condition, substrate protein lysine ε-amino group propionyl group, forming a derivatized propionylated lysine. For lysine monomethylation modification, since lysine ε-amino group has also an additional propionyl anhydride reaction site, thus propionylated reaction can also take place, forming a derivatized propionyl methylation lysine (FIG. 1a). the ε-amino group on dimethylation modification or trimethylation modified lysine has no propionyl anhydride reaction site, the propionyl derivatization reaction can not a take place (Garcia, B. A. et al. Chemical derivatization of histones for facilitated analysis by mass spectrometry. Nature protocols 2, 933-938 (2007)). When in vivo lysine monomethylation modification in vitro derivatization reaction lysine propionyl methylation modification, space structure of the modifying group greatly increases, it is more easily be specifically identified by the antibody, Therefore, in theory it is able to prepare an antibody specifically recognizing the propionyl methylated lysine, identify propionylation derivation reaction lysine monomethylation modified polypeptide (FIG. 7c).

Garcia and Hunter firstly using lysine propionylation into histone (i.e. extract histone, then in modification study lysine propionylation is conducted to the 5 types of histones after extraction) (Garcia, B. A. et al. Chemical derivatization of histones for facilitated analysis by mass spectrometry. Nature protocols 2, 933-938 (2007)) such chemical method in a more complex system, such as cell or tissue lysate total protein. However, the present invention firstly conducts extraction of the total protein from cell or tissue, then conduct in vitro propionylation reaction. After protease lysis, total protein lysine monomethylated group is analyzed using the method of antibody enrichment along with mass spectrum analysis (the detailed description can be seen later).

In one preferred embodiment, the K562 cell lysate total protein used in the present invention reacts with propionic anhydride under pH=8.5. After reaction, digested by trypsin in a pH 7.2 ammonium carbonate-sodium bicarbonate buffer solution, mass spectrum analysis lysine propionylation reaction polypeptide. If the in vitro propionylation reaction is completed, the ratio containing the unmodified lysine polypeptide is very low. Identify result indicates that, after propionylation reaction, only 7 polypeptides (1.4%) in all detected 2,556 polypeptides contain unmodified lysines, this shows that the in vitro propionylated reaction used in the present invention has very high efficiency to a complex total protein system (FIG. 9).

Regardless of the cells are labelled with $^{12}CH_3$-Met or $^{13}CD_3$-Met, the labelled $^{12}CH_3$- or $^{13}CD_3$-lysine monomethylation modification, propionylation derivatization reaction can occur, to produce propionyl $^{12}CH_3$-lysine or propionyl $^{13}CD_3$-lysine. propionylation derivatization reaction to determine or quantify lysine monomethylation modification, another reason of using $^{13}CD_3$-Met labelling is because mass displacement in propionyl $^{12}CH_3$-lysine is same as lysine butyryl (70.0440 Da), but the propionyl $^{13}CD_3$-lysine has unique 74.0640 Da of mass displacement, in mass spectrum analysis the lysine butyryl modification can be distinguished in vivo, accurately identifying the lysine monomethylation modification.

Enrichment and Preparation of Lysine Propionyl Methylation Polypeptide Pan Antibody As described in phosphorylation and lysine acetylation study, affinity enrichment is the key step of studying protein modification global analysis. Because the difference of physicochemical properties on monomethylated modified lysine and unmodified lysine is very small, it is very difficult to separate methylation modified lysine polypeptide phosphorylated polypeptide by chemical methods such as Immobilized Metal Affinity Chromatography (IMAC). In addition, it is also difficult to prepare lysine monomethylated antibody of high specific and certain affinity. To resolve this difficulty, the present invention has developed a novel method for enriching monomethylated polypeptide, this method includes the following three main steps: (1) reacting the lysine on the monomethylated ε-amino group with propionic anhydride, forming a propionyl methylated ε-amino group derivative; (2) using specific propionyl methylation lysine to antibody enrich the polypeptide containing the propionyl methylated lysine; (3) HPLC and mass spectrum analysis of enriched polypeptide, identifying the sequence of antibody enriched polypeptide and confirm the modification site.

In vitro lysine propionylated derivatization reaction is the premise of based on antibody enrichment method, its theory and importance have been described in detail. It is also important that the method of the present invention requires specific propionyl methylation lysine pan antibody. Since the propionyl methylation group, therefore the pan antibody for preparing propionyl methylation lysine is simpler than the pan antibody for preparing the monomethylated lysine. In order to conform this assumption, using propionyl monomethylated lysine (FIG. 7D) KLH coupling immunize rabbit, anti-propionyl methylation lysinepan antibody is purified from the rabbit serum. Using a dot blot method containing propionylated lysine (Kpr), butyrylated lysine (Kbuty), butenoylated lysine (Kcr), monomethylated lysine (Kme1), di-methylated lysine (Kme2) and tri-methylated lysine (Kme3) polypeptide library at fixed position to determine antibody specificity (FIG. 7c). The results indicate the specificity of propionylation methylated lysine pan antibody propionyl methylated lysine polypeptide library is higher than another polypeptide library 100-fold or more. Although the structure of propionyl methylated lysine is similar with the structure of propionylated lysine and butyrylated lysine, but the detection result of dot blot indicates the propionyl methylation lysinepan antibody used in the present invention have high affinity and specificity, can be used in enrichment of lysine propionyl methylated polypeptide.

Affinity enrichment of the modified polypeptide based on antibody is one of main methods of high-throughput protein modification, e.g. it has extensive allocation in lysine acetylation study. After the total protein extracted from cell or tissue undergoes in vitro propionylation reaction, lysine propionylation derivatized polypeptide can be produced via protease enzyme digestion, include lysine propionyl methylation derivatized polypeptide. In one preferred embodiment, the protease is primarily trypsin. Then, the specific propionyl methylation lysinepan antibody is covalently coupled with protein A agarose resin to prepare an antibody coupled resin, the antibody coupled resin is incubated in a specific buffer solution with the lysine propionylation derivatization polypeptide has more antigen-antibody specific affinity binding characteristics, lysine propionyl methylation derivatized polypeptide can affinity bond to the antibody resin. After the non-specifically bonded polypeptide was washed with a wash buffer, the lysine propionyl methylation derivatized polypeptide specifically bonded on the antibody can be eluted with an elution buffer with low pH. After drawn to dryness, Nano-HPLC-MS/MS mass spectrum analysis identifies lysine propionyl methylated derivatized polypeptide sequence and confirm the modification site.

Detection of Propionyl Monomethylated Lysine Polypeptide

Chemically modifying group modification substrate and polypeptide mass displacement, such as monomethyl modification-$CH_2$ group may substrate 14.0147 Da of mass displacement, but phosphorylation modification substrate 79.9663 Da of mass displacement. lysine methylation mass displacement some amino acid mass displacement, for example serine was mutated to threonine, aspartic acid was mutated to glutamic acid, valine was mutated to leucine or isoleucine, asparagines was mutated to glutamine. In addition, propionyl methylation butyrylated lysine same mass displacement. Lysine butyryl is also one modification method of in vivo protein. Thus, when presence of monomethylation modification or in vitro group modification in certain specific amino acid is detected, if there is no correct quality control, the identification of propionyl methylated polypeptide may have false positive result. Therefore, the present invention can avoid the false positive results by using existing $^{13}CD_3$ isotope labelled methylation polypeptide metho.

For example, when identifying presence of monomethylation modification in lysine, when the cells were cultured by the isotope labelling method, the methionine $^{12}CH_3$ in routine culture medium was replaced to $^{13}CD_3$. In cells, lysine methylation precursor-S-adenosine methionine (SAM) is converted from methionine. Therefore, in cell lysine methylation, $^{13}CD_3$ methionine is converted to $^{13}CD_3$S-adenosine methionine ($^{13}CD_3$-SAM), such that 18.027 Da of mass displacement occurred in the lysine. $^{13}CD_3$-methylated lysine in vitro propionylation 74.0640 Da mass displacement. Mass spectrometry detection can distinguish such unique mass displacement with any other known protein modification type or amino acid mass displacement. In one example of the present invention, ne propionyl methylation polypeptide is identified from HSP90 protein (FIG. 1c), by 74.0640 Da of mass displacement, may confirm occurrence of propionyl methylation modification at the lysine at the 3rd position of the polypeptide, thereby deduce lysine monomethylation modification occurring on the site.

To further validate reliability of this method, combining the $^{13}CD_3$ methionine labelling method with SILAC method. During experiment, HeLa cells were cultured in $^{12}CH_3$-methionine and $^{13}CD_3$ methionine culture medium, methyl group is labelled. After labelling, same amount of two types of lysis protein is mixed, in vitro propionylation derivatization reaction, then trypsin digestion preparation enzymolyzed polypeptide. In order to reduce complexity of the sample and to increase the throughput of mass spectrum analysis, the polypeptide was separated by preparative HPLC, totally 20 polypeptide components are prepared. For each of the prepared polypeptide components, affinity enrichment to the propionyl methylation polypeptide is conducted using pan propionyl methylated lysine pan antibody, after enrichment polypeptide is eluted, and nano-HPLC/MS/MS analysis is conducted.

During mass spectrum analysis, lysine propionyl methylation modification of polypeptide methyl group hydrogen ion and $^{12}C$ ion are respectively replaced by deuterium(D) ion and $^{13}C$ ion, 4.002 Daltons of mass displacement will occur (FIG. 9A). In order to ensure accuracy of the analysis, all spectrometry data analysis software Mascot MS/MS spectrum further manual check. By using such method, 183 propionyl methylation modified polypeptides of high confidence were identified from HeLa cells (FIG. 3C). In 20 enzymolyzed polypeptide components, the enrichment efficiency is between 3% and 41% (FIG. 9D). By manual check of initial data, where 180 propionyl methylation modified polypeptides have a pair of precursor ions, corresponding to 190 methylation modification sites of 162 types of protein. Only two polypeptides contain "heavy" ion, one polypeptide has "light" ion. This demonstrates $^{13}CD_3$ replace methyl group method monometylation site analysis and erase the false positive result are reliable. It also demonstrates such it is reliable to use such a method in identifying monomethyl modified polypeptide.

The Range of Protein Lysine Monomethylated

Then using the $^{13}CD_3$ methionine labelling method to detect K562 cells (chronic myeloid leukemia cells), SW620 cells (Colon cancer cells), A549 cells (lung cancer cells) and SMM7721 cells (liver cancer cells) 4 types of lysine monomethylation modification human derived tumor cells. Polypeptide identification using strict 1% false positive rate and eliminate the polypeptide having MASCOT score below 20, and manually check the accuracy of each spectrum. After above-described strict quality control, the present invention totally identified 448 non-redundant lysine monomethylation modified polypeptides in four tumor cells, corresponding to 460 sites in 403 proteins. In these polypeptide, 73% of Mascot score is higher than 30 (FIG. 10A). By retrieving a public Uniprot database, identify most of monomethylation site has not been reported. The complete list of the monomethylated lysine polypeptide and protein identified by the present invention are seen in FIG. 7.

Lysine monomethylation modification of core histone have been widely studied, thus is can be used a good positive control. In agreement with prediction, the present invention totally identified 12 histone monomethylation modification sites. In addition to identifying K4, K9, K27, K36, K79 of extensively studied histone H3 and histone H4K20 several methylation sites, identify seldom studied Histone H3 of K18 monomethylation modification site. Because 5 types of cells are present in these lysine monomethylation modification site, the present invention identify these sites demonstrate such detection lysine monomethylation modification method is stable and reliable. It is important that, using the present invention aid method, the inventors also identified some new modification sites from many known monomethylation modification protein. Such as WIZ protein, in addition to the identifying reported lysine K976 site, two new lysine monometylation sites of K1321 and K1463 are also identified.

In order to further validate effectiveness of the present invention method, the inventors then analyzed lysine monomethyl modification in human liver cancer tissue, to study substrate range of the lysine monomethylation modification in clinical tissue compared with above 5 types of tumor cell identified lysine monomethylation modification data, the results indicate that 32 monomethylation sites in liver cancer tissue in 29 monomethylation modification polypeptide has these 5 types of cells, include 20 new lysine methylation sites and lysine monomethylation site of 6 histone H3 (FIG. 13), further indicate reliability of the present invention method.

Validation of Newly Identified Lysine Monomethylation Modification Site

Since lysine monomethylation modification site of most of non-histones specific antibody cannot be obtained commercially, unable to verify the site by biochemical method of western blotting identified by Mass Spectrometry. Therefore, the present invention validates mass spectrometry identify lysine monomethylation modified polypeptide method by using synthesizing the corresponding lysine monomethylated modified polypeptide. Mass spectrometry identifying-cell lysine monomethylated polypeptide corresponding artificially synthesized modified polypeptide, under the same mass spectrum analysis condition, should obtain the same secondary mass spectrum (MS/MS), this is the same criteria for polypeptide verification. For this, from the polypeptides of Mascot score being 20 to 60, any chosen 9 mass spectrometry identified propionyl monomethylated polypeptide sequence and artificially synthesized. Taking K562 cell CDC5L protein K114 site identifying propionyl methylation modification as example, by artificially synthesized LANTQGK$_{pr+me}$K$_{pr}$AK$_{pr}$ (SEQ ID NO: 9) polypeptide mass spectrum analysis, indicate after synthesis of polypeptide antibody affinity enrichment, mass spectrometry identifies 4 Da of difference by polypeptide isotope labelling, has completely same secondary mass spectrum (FIG. 11A). Except for verification by synthetic polypeptide method, in cells verification CDC5L protein lysine monomethylation modification. By immunize precipitated endogenous CDC5L protein was purified from the cultured K562 cells, then mass spectrum analysis. As described above, using $^{13}CD_3$-labelled methyl group, then mass spectrum analysis purification CDC5L protein. K164 monomethylated polypeptide LANTQGK$^{13}CD_{3-me}$K (SEQ ID NO: 10) is identified from purified CDC5L protein in cell. In order to further validate this site, by analyzing the spectrum of the corresponding synthetic polypeptide, indicate that in cell polypeptide except for 4 Da of difference by isotope labelling, essentially identical (FIG. 11B).

The same verification method also approve that the secondary mass spectrum of PVK$_{pr+me}$GAYR (SEQ ID NO:7) peptide identified from KHDRSB1 protein in HeLa cells (FIG. 12A) identical with secondary mass spectrum of artificially synthesized PVK$_{pr+me}$GAYR (SEQ ID NO:7) peptide (FIG. 6A); in secondary mass spectrum (FIG. 12C) of K562 cell EIF4H protein identified K$_{pr+me}$GGPDDR (SEQ ID NO:8) peptide, identical with secondary mass spectrum of corresponding vitro synthesis polypeptide K$_{pr+me}$GGPDDR (SEQ ID NO:8) (FIG. 12D). This demonstrates the method provided by the present invention can identify the lysine monomethylation modification at high confidence.

EXAMPLES

The present invention identified or quantified lysine monomethylation modification of peptide or protein in cells or tissues by using specific embodiments, such example is only how the method of the present invention is carried out, do not expose any limitation to the present invention. Those skilled in the art can make any improvements and changes to the present invention without departing from the gist of the present invention, but such change are all included in the scope of the claims of the present invention.

The reagents used in Example 1-2 of the present invention are as follow:

TABLE 1

| English name | Chinese name | Company | Batch number |
| --- | --- | --- | --- |
| KLH | hemocyanin | Pierce | 77600 |
| Sulfo-NHS | N-hydroxysulfosuccinimide | Thermo | 24510 |
| EDC | 1-(3-dimethylaminopropyl)-3-ethyl carbodiimide hydrochloride | Thermo | 22980 |
| DMSO | dimethyl sulfoxide | Solarbio | D8370 |
| Protein G | Protein G | Genscript | L00209 |
| Protein A | Protein A | Genscript | L00210 |
| PVDF membrane | polyvinylidene fluoride membrane | Millipore | ISEQ00010 |
| HRP Substrate | horseradish peroxidase Chemiluminescent substrate | Millipore | WBKLS0500 |
| SulfoLink Coupling Resin | SulfoLink coupled resin | Pierce | 20402 |
| Ultra TMB-ELISA Substrate | 3,3',5,5'-tetramethyl-benzidine substrate | Pierce | 34028 |

In Example 1-2 of the present invention, the formulations of various solutions are as follows:

TABLE 2

| Name | Ingredients | PH |
| --- | --- | --- |
| Wash buffer solution A | 1M NaCl, 0.5% NP-40 | 7.2-7.4 |
| Wash buffer solution B | 1M NaCl | |

TABLE 2-continued

| Name | Ingredients | PH |
|---|---|---|
| elution buffer solution | 0.1M Glycine | 3.0 |
| Neutralization buffer solution | 1M Tris-HCl | 8.5 |
| coupled buffer solution | 50 mM Tris | 8.5 |
| blocking buffer solution | 50 mM L-cysteine-Hcl | |
| Phosphate buffer solution(PBS) | 137 mM NaCl | 7.2 |
| TBST wash solution | 20 mM Tris, 0.2% Tween | 7.4 |
| KLH solution | KLH protein dissolved in activated buffer solution | |

Example 1: Development of Polyclonal Antibody

1. Monomethyl propionylated lysine small molecule synthesis (Lys(me-prop)-OH) synthesis the lysine ε-residue is linked with methyl propionyl group, NHFMoc was the protective group).
Synthesis Route:

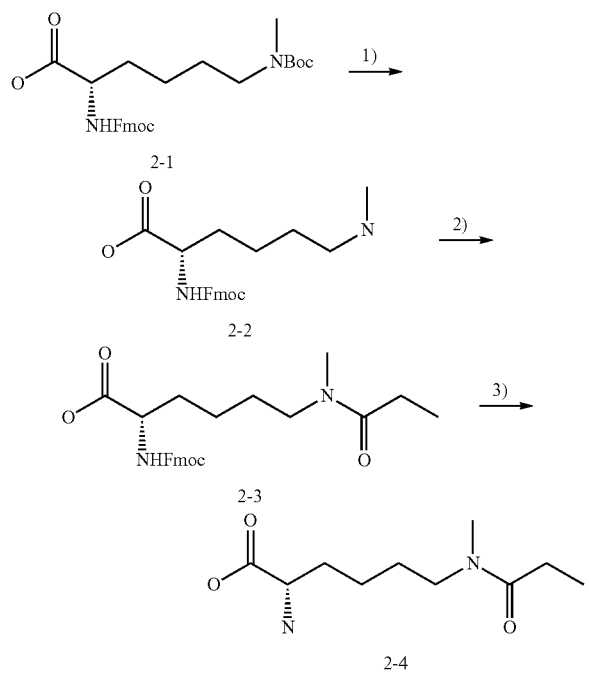

1) 14 g (0.029 mol) of 2-1(N'-tert-butyloxycarbonyl-N-fluorenylmethoxycarbonyl-N'-methyl-L-lysine, $C_{27}H_{34}N_2O_6$) was dissolved in dichloromethane (DCM), newly prepared HCl gas was continuously introduced at normal temperature for 1.5 hours, then the reaction was continued in a strong acid of HCl at normal temperature for 5 hours, the completion of reaction was confirmed by thin layer chromatography TLC; spin dried at 50° C. under 0.03 MPa, then 14.7 g of viscous solid was obtained, then silica gel column chromatography was conducted (eluant ratio: DCM-DCM:MeOH=50:1-DCM:MeOH=20:1), to obtain 10.8 g (0.0283 mol) of 2-2(N-fluorenylmethoxycarbonyl-N'-methyl-L-lysine, $C_{22}H_{26}N_2O_4$).

2) to 10.8 g 2-2 30 mL acetone was added and dissolve, and 70 mL of 1.1 M solution of $NaHCO_3$ in water was added, then stirred at room temperature for 2 hours (thoroughly stirred, to remove the HCl bonded with the raw material), in ice water bath 50 mL of acetone solution dissolving 3.93 g (0.03 mol) propionic anhydride was slowly added, and reacted for 1 hour; after completion of the reaction, pH was adjusted to about 3.0 with a 2 N hydrochloric acid, and 100 mL of DCM was added to extract twice, the organic phase was removed at 50° C., via 0.03 MPa rotary evaporation to obtain 12.4 g of a viscous solid, silica gel column chromatography (eluant ratio: DCM-DCM:MeOH=50:1-DCM:MeOH=30:1) was conducted to obtain 10 g (0.0228 mol) 2-3(N'-propionyl-N-fluorenyl-methoxycarbonyl-N'-methyl-L-lysine, $C_{25}H_{30}N_2O_5$).

3) to 10 g 2-3 70 mL of N,N-dimethylformamide (DMF) and 45 mL tetrahydrofuran (THF) were added and dissolved, 6 mL (0.061 mol) of piperidine was added, stirred at normal temperature overnight, completion of reaction was confirmed by TLC; the solvent was evaporated to dryness by vacuum distillation with an oil pump (0.88 kPa), to obtain 8 g mixed product, via silica gel column chromatography (eluant ratio: DCM-DCM:MeOH=50:1-DCM:MeOH=30:1), to obtain 3.4 g (0.0147 mol) of pure esterified product; 0.585 g of sodium hydroxide, 35 mL of water, and 35 mL of methanol were added for hydrolysis, and reacted in an ice water bath for two hours, after complete hydrolysis of the esterified product the pH was adjusted with 2 N HCl to 3.0. The solvent was spin dried at 50° C. under 0.03 MPa, and 20 mL of ethanol dissolved product was added, after filtration the filtrate was spin dried, to obtain 2.6 g of a final product 2-4 (Lys(me-prop)-OH, N'-propionyl-N'-methyl-L-lysine $C_{10}H_{20}N_2O_3$).

2. Coupling of monomethyl propionylated lysine compound with carrier protein KLH for preparation of immunogen
1) 10 mg KLH was dissolved in 1 mL MES buffer solution;
2) 0.4 mg of EDC and 1.1 mg of Sulfo-NHS were added separately; mixed well, and reacted at room temperature for 15 minutes;
3) then 1.4 μL of 3-mercaptoethanol was added, reacted for 10 min, then the pH was adjusted to 7.4 with PBS;
4) 2 mg of Lys(me-prop) compound was dissolved in PBS, then added into the KLH solution activated in step (3), mixed well, and reacted at room temperature for two hours;
5) then 50 mM Tris was added and reacted for 15 minutes, dialyzed in PBS solution at 4° C. overnight.

3. Animal Immunization Procedure
1) 8 weeks old New Zealand Rabbit, subcutaneously injected at multiple spots;
2) first immunization: 500 μL KLH coupled small molecule immunogen of concentration being 0.8 mg/ml was mixed with same volume of complete Freund's adjuvant to be emulsified, subcutaneously immunized at multiple spots on the back;
3) after 3 weeks, 500 μL rabbit KLH coupled small molecule immunogen having a concentration of 0.4 mg/ml was mixed with the same volume of non-complete Freund's adjuvant to be emulsified, subcutaneously injected at multiple spots on the back;
4) every 2 weeks, immunized once according to the dose and method of Step 3;
5) 10 days after the fourth immunization, 1 ml of serum was taken out, the serum titer was detected by ELISA method. If the serum titer was more than 30 thousand, by blood collection from heart. If the serum titer was unqualified, the step 4 was repeated until the serum titer was more than 30 thousand.

4. Purification of Polyclonal Antibody

Purification of total IgG with protein A resin:

1) 10 mL of serum with titer more than 30 thousand was centrifuged at 10000 r/min for 10 minutes, the supernatant was withdrawn, and filtered with a 0.45 μm microporous filter membrane;

2) 3 ml of protein A resin was balanced at room temperature for 1 hour, the resin was wash with 4-fold column volume of phosphate buffer solution (PBS, pH=7.2);

3) 20 ml of filtered serum was loaded to a column containing protein A resin, and at incubated with Protein A column at room temperature for 90 minutes, then placed for 15 minutes;

4) the column was washed once with 10-fold column volume of wash buffer A respectively, and washed once with 15-fold column volume of PBS;

5) eluted by 5-fold column volume of elution buffer, then a neutralization buffer was added, dialyzed at 4° C. in PBS overnight;

6) IgG was ultra-filtrated to a concentration of 5-10 mg/ml.

Preparation of Antigen Polypeptide-Coupled Column

1) SulfoLink Coupling Resin was balanced at room temperature for one hour, mixed well and withdraw 5 ml into a chromatography empty column, washed with 4-fold column volume of coupled buffer twice;

2) 5 mg of antigen polypeptide was weighed, dissolved in coupled buffer solution respectively, and added to SulfoLink Coupling Resin Chromatography Column and mixed well, and incubated at room temperature for 15 minutes;

3) placed for 30 minutes, the column was washed with 15-fold column volume of coupled buffer solution;

4) added 1-fold column volume blocking buffer solution, incubated at room temperature for 15 minutes, then the column was washed with wash buffer solution B of 6-fold column volume;

5) obtained polypeptide 1 coupled column and polypeptide 2 coupled column, respectively.

Antibody Affinity Purification with Antigen Polypeptide 5 mg of Protein A pre-purified ultrafiltration IgG was added into antigen polypeptide coupled column, incubated at room temperature for 2 hours; the effluent wad discarded, the column was respectively washed with a 5-fold column volume of wash buffer and 10-fold column volume of PBS, then the antibody is purified according to the following steps:

1) eluted by 4-fold column volume elution buffer;

2) to the diluent a neutralization buffer was added, and dialyzed in a dialyzing bag at 4° C. PBS overnight;

3) IgG was ultrafiltrated to concentration of 5-10 mg/ml;

4) after the above-described ultrafiltration, the IgG was added into a polypeptide coupled column, incubated at room temperature for 30 minutes, and the effluent was collected, that was the purified antibody.

5. Dot Blot Detection:

1) the polypeptides listed in Table 3 and 4 were dissolved in water, to prepare a polypeptide solution with an initial concentration of 100 ng/μL;

2) a PVDF membrane of appropriate size was cut out, treated with absolute methanol for 40 seconds, washed in deionized water for three times, air dried for 2 minutes;

3) the polypeptide solution with an initial concentration of 100 ng/μL was further diluted to 20 ng/μL and 4 ng/μL respectively. Then the samples were successively applied, 1 μl/pot, dried for 10 minutes then put into a 6-well plate;

4) blocked with a 5% skimmed milk powder at room temperature for 60 minutes, rinsed with TBST wash solution twice, 5 minutes/time;

5) the antibody was diluted with 5% skimmed milk powder, incubated at room temperature for 1 hour, rinsed with TBST wash solution for three times, 10 minutes/time;

6) goat anti-rabbit HRP-labelled antibody was diluted with 5% skimmed milk powder at room temperature for 45 minutes, rinsed with TBST wash solution for three times, 10 minutes/time;

7) a chemiluminescent indicator liquid was evenly laid onto the membrane, incubates for 5 minutes then exposed to light, the results are seen in FIGS. 1 and 2.

TABLE 3 the sequence of the polypeptide used in the dot blot assay of FIG. 1 and 4 (K* represents the modified lysine, where X is any amino acid among 19 common amino acids except for cysteine)

| Number | Name | Sequence |
|---|---|---|
| 1 | Lysine methyl propionylated polypeptide library | CXXXXXK* (methyl propionyl) XXXXX (SEQ ID NO: 11) |
| 2 | Lysine methyl propionylated GG polypeptide | CEGRGDSGGG K* (methyl propionyl) GGSG (SEQ ID NO: 12) |
| 3 | Methyl propionylated lysine small molecule compound | K* (methyl propionyl methylpropionyl) |
| 4 | KLH coupled methyl propionylated lysine small molecule compound | KLH- K* (methyl propionyl) (SEQ ID NO: 13) |
| 5 | Lysine propionylated peptide library | CXXXXX K* (propionyl)XXXXX (SEQ ID NO: 14) |
| 6 | Lysine propionylated GG polypeptide | CEGRGDSGGG K* (propionyl)GGSG (SEQ ID NO: 15) |

TABLE 3-continued the sequence of the polypeptide used in the dot blot assay of FIG. 1 and 4 (K* represents the modified lysine, where X is any amino acid among 19 common amino acids except for cysteine)

| Number | Name | Sequence |
|---|---|---|
| 7 | Lysine methyl acetylated polypeptide library | CXXXXX K*(methylethoxylated)XXXXX (SEQ ID NO: 16) |
| 8 | Lysine methyl acetylated GG polypeptide | CEGRGDSGGG K*(methylethoxylated)GGSG (SEQ ID NO: 17) |
| 9 | Lysine methyl butyryl polypeptide library | CXXXXX K*(methylbutyryl)XXXXX (SEQ ID NO: 18) |
| 10 | lysinemethylbutyryl GGpolypeptide | CEGRGDSGGG K*(methylbutyryl)GGSG (SEQ ID NO: 19) |
| 11 | unmodified lysine polypeptide library | CXXXXXKXXXXX (SEQ ID NO: 20) |
| 12 | unmodified lysine GGpolypeptide | CEGRGDSGGGKGGSG (SEQ ID NO: 21) |
| 13 | KLH | KLH |

TABLE 4 the sequence of polypeptides used in the dot blot assay of FIG. 2 and FIG. 5 (K* represents the modified lysine, where X was any amino acid of 19 common amino acids except for cysteine)

| Number | Name | Sequence |
|---|---|---|
| 1 | Lysine methyl propionylated polypeptide library | CXXXXX K* (methyl propionyl)XXXXX (SEQ ID NO: 23) |
| 2 | Lysine propionylated polypeptide library | CXXXXX K*(propionyl)XXXXX (SEQ ID NO: 24) |
| 3 | Lysine butyryl polypeptide library | CXXXXX K*(butyryl)XXXXX (SEQ ID NO: 25) |
| 4 | Lysine monomethylated polypeptide library | CXXXXX K*(methyl)XXXXX (SEQ ID NO: 26) |
| 5 | Lysine di-methylated polypeptide library | CXXXXX K*(2 methyl)XXXXX (SEQ ID NO: 27) |
| 6 | Lysine tri-methylated polypeptide library; | CXXXXX K*(3 methyl)XXXXX (SEQ ID NO: 28) |

Dot blot detection indicate, by the monomethyl propionylated lysines mall molecule designed by the present invention, the obtained polyclonal antibody as the antigen can specifically identify lysine methyl propionylated polypeptide library, lysine methyl propionylated GG polypeptide, monomethylated propionylated lysine small molecule and KLH coupled monomethylated propionylated lysine small molecule, but cannot identify other types of lysine modificated polypeptides (FIG. 1), this demonstrated that the antibody had a good specificity. The results of FIG. 2 indicated that the developed monomethylated propionylated lysine polyclonal antibody can identify 4 nanogram of lysine methyl propionylated polypeptide library, but do not identify similar structure until 100 nanogram other modified lysine-polypeptide library, this indicated the sensitivity of the developed antibody, also further indicated the specificity of this polyclonal antibody.

6. ELISA Assay:

1) coating: the lysine methyl propionylated polypeptide was diluted with deionized water to $1\times10^{-3}$ mg/mL, 50 μl/well, at 4° C. coating enzyme label plate overnight;

2) blocking: on the next day with TBST washed with TBS once, 5 minutes/time, 200 μl/well, beated to dry, blocked with 70 μl of 1% BSA/TBS for 45 minutes;

3) competition: the purified lysine monomethylated propionyled polyclonal antibody was diluted with a PBS 1:200, then 0 nanogram, 10 nanogram, 50 nanogram and 100 nanogram of the polypeptides listed in Table 1 and 2 were added respectively, and reacted at 4° C. overnight;

4) purified lysine monomethylated propionyled polyclonal antibody was added: at the next day centrifuged at 3000×g and supernatant, diluted to 10-fold, added to enzyme label plate, 50 μl/well, and incubated at 26° C. for two hours.

5) HRP labeled goat anti-rabbit IgG secondary antibody was added: washed with dTBST for 3 times, 5 minutes/time, 200 μl/well, beated to dryness, and a secondary antibody was added, diluted 1:10000 (1% BSA/TBS), 50 μl/well, and incubated at 26° C. for 45 minutes.

6) adding substrate: according to the method of Step 5, rinsed with TBST for three times, beated to dryness. A TMB developing substrate was added 50 μl/well, and reacted at 26° C. for 30 minutes;

7) termination: 2M sulfuric acid was added, 50 μl/well.

8) color developing: absorbance was determined by a microplate reader $OD_{450}$.

As can be seen from the results of FIG. 3, the purified antibody competition, the amount of lysine methyl propionylated polypeptide library, lysine methyl propionylated GG polypeptide, antibody reacted with pre-coated lysine methyl propionylated polypeptide and the ELISA signal was also decreased, other modified lysine polypeptide competition, the antibody was reacted with the pre-coated lysine methyl propionylated polypeptide ELISA signal remained identical, this further demonstrated the specificity of the developed lysine monomethylated propionylated polyclonal antibody.

Example 2: Development of Monoclonal Antibody

1. Determination and Synthesis of Antigen Polypeptide Sequence

The sequence of the polypeptide used in immunization was CEGRGDSGGGK*GGSG (SEQ ID NO:2), where the lysine (K) residue at 11th position was coupled with monomethyl group (me) and propionylation (prop) group.

Control polypeptide sequence (control sequence, not be used in immunization): CEGRGDSGGGKGGSG (SEQ ID NO:21), lysine (K) residue at the 11th position had no any group modification.

Synthetic steps of the Antigen polypeptide were as follow:

A. Synthesis of Propionylated Monomethyl Lysine Raw Material (Fmoc-Lys(me-prop)-OH) (i.e. lysine ε-Residue is Coupled with Monomethyl Propionyl Group)

1) preparation of chloroformic acid benzyl-lysine (trifluoroacetic acid, methyl)-methyl ester (Z-Lys(TFA, me)-Ome): chloroformic acid benzyl-lysine (trifluoroacetic acid)-OH(Z-Lys(TFA)-OH), methyl iodide ($Me_2I$), $K_2CO_3$ and DMF were reacted and fluxed together, the reaction solution was drawn out for mass spectrometry detection to confirm completion of synthesis;

2) generation of chloroformic acid benzyl-lysine(methyl)-OH(Z-Lys(me)-OH): the Z-Lys(TFA, me)-Ome generates in Step 1 was reacted with LiOH saturated solution at pH more than 12.0, the reaction solution was drawn out to mass spectrometry detection to confirm completion of synthesis;

3) generation of chloroformic acid benzyl-lysine(methyl-propionyl)-OH(Z-Lys(me-prop)-OH):

Z-Lys(me)-OH, propionic anhydride and triethylamine were reacted under pH=9.0, the reaction solution was drawn to mass spectrometry detection. After completion of the reaction, acidified, abstracted with ethyl acetate extract. And concentrated to an oily substance.

4) generation of H-Lys(me-prop)-OH: Z-Lys(me,prop)-OH obtained in Step 3 was dissolved in methanol, and Pd/C was added, hydrogen gas was introduced in, the reaction was tracked by TLC. After completion of the reaction, filtered, the filtrate was concentrated to obtain a solid, then washed with ethyl ether for 4 times, and dried.

5) generation of Fmoc-Lys(me-prop)-OH: H-Lys(me-prop)-OH, fluorenylmethoxycarbonylsuccinimide (Fmoc-OSu) satured $NaHCO_3$ solution and acetone were reacted under pH=9.0, the reaction was tracked by TLC. After completion of the reaction, routinely treated, acidified, the product was extracted with ethyl acetate, dried and concentrated to an oily substance.

B. Synthesis of Antigen Polypeptide

The polypeptide synthesis was conducted on ABI 433 polypeptide synthesizer.

1) Resin swelling: N-fluorenylmethoxycarbonyl-glycine resin (Fmoc-Gly-Wang resin) was immersed in dichloromethane for 15 minutes, after swelling of the resin, dichloromethane was withdrawn;

2) Removal of amino protection: volume 1:4 hexahydropyridine/DMF solution was added, bubbled with nitrogen gas, reacted for two times, the time is 5 minutes and 15 minutes, after reaction completion the resin was washed with DMF for 9 times. A small amount of resin added developer ABC 2-3 drops (A solution: ninhydrin/absolute ethanol solution; B solution: pyridine; C solution: phenol/absolute ethanol solution) and heated at 100° C. for 3 minutes, the color of the solution and resin were blue (some amino acids was purple red), it may be determined that the amino protection has been removed.

3) Condensation reaction: Fmoc-Gly-OH and 1-hydroxybenzotriazole (HOBT) were added, dissolve with an appropriate amount of DMF, DIEA was added, nitrogen gas was bubbled, and reacted for one hour, after completion of the reaction the resin was wash with DMF for 6 times. Small amount of resin was taken out for color developing, the method is same as Step 2, the color of the solution and the resin should be colorless, confirming the completion of reaction.

4) Step 2-3 was repeated, successively polypeptide sequence amino acid, until completion of the sequence, the resin was immersed in dichloromethane and ethyl ether, and drawn to dryness 5) Polypeptide was cut off from the resin: TFA was added, reacted in a thermostatic shaking table for two hours, rotation speed of the shaking table was 110 rotation/minute, the temperature was 25° C.

6) Precipitating the crude product: the resin wad filtered off, to the filtrate added water-free ethyl ether was added, centrifuged by a centrifuge to obtain a solid, water free ethyl ether was added and washed, centrifuged again, repeated for several times, then dried to obtain a crude polypeptide.

2. Preparation of Polypeptide Total Antigen 1) 20 mg of KLH was dissolved in 2 mL of 5 mM EDTA/$H_2O$;

2) After 5 mg S μL fo-SMCC was completely dissolved in 40 μL of DMSO, 160 μL of PBS was added, mixed well;

3) Under stirring, S μL fo-SMCC solution was dropwise added to the KLH solution. Placed at room temperature for one hour, then the above-described activated KLH solution was dialyzed in 1 L of pre-warmed PBS at 4° C. for 1 hour; after the solution was changed, dialyzed at 4° C. for 2 hours, repeated once; 5 mg of antigen polypeptide was weighed, dissolved in 100 μL DMSO, and 400 μL of PBS was added, mixed well, then 500 μL of above-described dialyzed activated KLH solution was added, put in a 4° C. refrigerator overnight;

4) Above-described KLH linked antigen polypeptide cross-linked complex was dialyzed in 4 L of PBS solution at 4° C. overnight;

5) On the next day, the KLH-antigen polypeptide was removed out and stored at −20° C.

3. Procedure of Animal Immunization 1) 6-8 weeks old Balb/c mouse, subcutaneously injected at multiple spots;

2) In first immunization, 100 µL of 1 mg/mL immunogen was mixed with same volume of complete Freund's adjuvant to be emulsified, and subcutaneously immunized at multiple spots on the back;

3) After 3 weeks, 100 µL of 0.5 mg/mL immunogen were mixed with same volume of non-complete Freund's adjuvant to be emulsified, subcutaneously injected at multiple spots on the back;

4) Every 2 weeks, according to dose and method of Step 3 to immunize;

5) 10 days after the fourth immunize, 20 µL serum was taken out, the serum titer was detected by ELISA method. If the serum titer was unqualified (serum titer should be more than 30 thousand), Step 4 was repeated until the serum titer was more than 30 thousand.

4. Cell Fusion

1) After the mouse was killed by pulling neck, the spleen was removed out, grinded on a steel wire, the spleen cells were collected, DMEM culture medium was washed twice, and counted;

2) sp2/0 myeloma cells were collected into a 50-ml centrifuge tube, and centrifuged for 5 minutes, counted;

3) Spleen cells and sp2/0 cells at a ratio of 1:4 were mixed and centrifuged and collected;

4) The culture medium was poured completely, the bottom of the centrifuge tube was knocked, to make the cell precipitate to be loose;

5) 1 ml of polyethylene glycol (PEG) was added along centrifuge tube wall with a Pasteur pipet, stirred for 60 seconds, then 30 ml of pre-heated culture solution was added. The lid was covered, mixed well, centrifuged, and culture medium was poured completely;

6) Added fresh HAT culture medium suspended cell were spread onto the 96-well cell culture plate;

7) Positive cell line was obtained by ELISA, subcloning twice, a series of stable positive cell fusion strains were obtained, e.g. collected in China General Microbiological Culture Collection Center, Collection Number 9109 的 PMT-001 cell line, this cell line can secret monoclonal antibody.

5. Production of Ascites 1) subcloning stable cell was enlarged cultured (e.g. collected in China General Microbiological Culture Collection Center, Collection Number 9109, PMT-001 cell line);

2) Balb/c mousse of over 8-week-old were peritoneally injected 0.5 ml of incomplete adjuvant; after 10 days, after the abdomen of mouse raised slightly, each mouse was immunized by 1×106 cells;

3) After 7 days ascites was collected, centrifuged at 12000×g, the fat was removed, and the supernatant was collected.

6. Purification of ascites 1) 15 ml of ascites was centrifuged at 12000×g for 10 minutes, filtered with a 0.45 µm filter membrane;

2) 5 ml of Protein G was loaded into the chromatography empty column, washed with 4-fold column volume PBS for one time, and balanced at room temperature for 30 minutes;

3) 15 ml of the ascites in Step 1 was added into protein G column, incubated at room temperature for 2 hours;

4) After placing 15 minutes, the ascites was discharged, the column was washed with PBS of 15-fold column volume;

5) Eluted with 6-fold column volume of glycine diluent, collected and neutralization buffer solution was added, dialyzed in PBS at 4° C. overnight.

7. Dot blot detection:

1) The polypeptides listed in Table 3 and 4 were dissolved in water, to prepare a polypeptide solution with an initial concentration of 100 ng/µL;

2) An appropriate size of a PVDF membrane was cut out, treated for about 40 seconds with absolute methanol, rinsed in a deionized water for 3 times, air dried for 2 minutes;

3) The polypeptide solution having an initial concentration of 100 ng/µL was further diluted to 20 ng/µL and 4 ng/µL. Then, the sample was applied successively, 1 µl/spot, dried for 10 minutes then put into 6-well plate;

4) Blocked with a 5% skimmed milk powder at room temperature for 60 minutes, rinsed twice with a TBST wash solution, 5 minutes/time;

5) The antibody was diluted with 5% skimmed milk powder, incubated at room temperature for 1 hour, rinsed with TBST washing solution for 3 times, 10 minutes/time;

6) Goat anti-rabbit HRP-labelled antibody was diluted with a 5% skimmed milk powder at room temperature for 45 minutes, rinsed with TBST wash solution for 3 times, 10 minutes/time;

7) A chemiluminescent indicator was evenly laid onto the membrane, incubated for 5 minutes then exposed to light, the results can be seen in FIGS. 3 and 4.

The dot blot detection indicate, the monoclonal antibody obtained by using the CEGRGDSGGGK*GGSG (SEQ ID NO:2) polypeptide designed by the present invention as the antigen can specifically identify lysine methyl propionylated polypeptide library, methyl propionylated lysine small molecule compound, lysine methylpropionylated GG polypeptide and KLH coupled methyl propionylated lysine small molecule compound, but cannot identify other types of lysine modified polypeptides (FIG. 4), this demonstrates that the antibody having a good specificity. The results of FIG. 5 indicated that the developed monomethylated propionylated lysine monoclonal antibody can identify 4 nanograms of lysine methyl propionylationpolypeptide library, but it cannot identify similar structure until 100 nanograms of other modified lysinepolypeptide library, this not only indicated the sensitivity of the developed antibody, but also further indicated the specificity of this polyclonal antibody.

8. ELISA detection:

1) Coating: CEGRGDSGGGK*GGSG (SEQ ID NO:2) antigen polypeptide was diluted with a deionized water to 1×10-3 mg/mL, 50 µl/well, the enzyme label plate was coated at 4° C. overnight;

2) Blocking: on the next day, washed with TBST once, 5 minutes/time, 200 µl/well, beated to dry, blocked with 70 µl of 1% BSA/TBS for 45 minutes;

3) Competition: the purified cation lysine monomethylated propionylated monoclonal antibody was diluted with PBS 1:200, then 0 nanogram, 10 nanograms, 50 nanograms and 100 nanograms of polypeptides listed in Table 1 and 2 were added respectively, and reacted at 4° C. overnight;

4) Adding purified lysine monomethylated propionylated monoclonal antibody: on the next day, centrifuged at 3000×g and the supernatant was removed, diluted to 100-fold, added into the enzyme labeled plate, 50 µl/well, and incubated at 26° C. for 2 hours.

5) HRP labeled goat anti-rabbit IgG secondary antibody was added: washed with TBST for 3 times, 5 minutes/time, 200 μl/well, beated to dry, secondary antibody was added, 1:10000 diluted (1% BSA/TBS), 50 μl/well, and incubated at 26° C. for 45 minutes.

6) Adding substrate: according to the method in Step 5, washed with TBST for 3 times, beated to dry. TMB developing substrate was added 50 μl/well, and reacted at 26° C. for 30 minutes;

7) Termination: 2M sulfuric acid was added, 50 μl/well.

8) Color development: absorbance was measured by microplate reader OD450.

As can be seen form the results of FIG. 6, purification antibody competition of lysine methyl propionylated polypeptide library, lysine methyl propionylation antigen polypeptide, antibody reacted with pre-coated lysine methyl propionylation antigen polypeptide and ELISA signal was also decreased, their modified lysine polypeptide competition antibody reacted with the pre-coated lysine methyl propionylated antigen polypeptide and ELISA signal remains unchanged, this further verify the specificity of developed lysine monomethylated propionyled monoclonal antibody.

Example 3: Methionine Stable Isotope Labelling, In Vitro Propionylation Derivatized Reaction Protein Enzymolyzed 3.1 Methionine Stable Isotope Labelling The cells used in the present invention include HeLa cell (cervical cancer cell line), K562 cell (chronic myeloid leukemia cell), SW620 cell (colon cancer cell), A549 cell (lung cancer cell) and SMM7721 cell (liver cancer cell), cultured in a RPMI or DMEM culture medium (Life Technologies, CA) was conducted methionine stable isotope labelling. Culture medium primarily contains the following ingredients: $^{12}CH_3$-methionine or $^{13}CD_3$-methionine (Sigma-Aldrich, MO), 10% dialyzed fetal bovine serum (v/v) (dialyzed FBS) (Life Technologies, CA) and 1×antibiotics (Thermo Scientific, MA) and other suitable cell growth nutrient elements. The cells were cultured in a culture medium at 37° C. and 5% CO2.

The key of stable isotope labeled is that labeling efficiency being more than 97%, nd mass spectrometry detection. According to cell every division 50% of $^{12}CH_3$— was replaced by $^{13}CD_3$- (under physiological state is $^{12}CH_3$—), after the cells were divided 6 generations, then in vivo 99% of $^{12}CH_3$— was replaced by $^{13}CD_3$-, meeting the table isotope labelling efficiency required by theory. During parallel "light" ($^{12}CH_3$-Met) or "heavy" ($^{13}CD_3$-Met) stable isotope cell labelling, when "heavy" ($^{13}CD_3$-Met) stable isotope labelling meets the requirement, "light" ($^{12}CH_3$-Met) or "heavy" ($^{13}CD_3$-Met) stable isotope labeled cell need to be cultured continuously until the required cell number (108) can extract enough protein for the subsequent experiments. When the cells were cultured to meet the requirement, if lysine mono-methyl modification identification was conducted in cell, such as in the cell only collect "heavy" ($^{13}CD_3$-Met) labeled cell and conductivity total protein extract. If quantitative analysis of lysine monomethyl modification was conducted in cells, the "light" ($^{12}CH_3$-Met) or "heavy" ($^{13}CD_3$-Met) labeled cell collect were mixed at equal quantity then the protein was extracted.

3.2. Extraction of the Total Protein in Labelled Cells

Labeled cells collected were washed with pre-cooled phosphate buffer (PBS) for 3 times, then the cells were lysis in a pre-cooled lysis buffer solution (8M urea dissolved in 2:1 0.1 M $NH_4HCO_3$ buffer solution (PH=8) and 0.1 M $NaHCO_3$ solution; 1× protease inhibitor (v/v)), finally incubated on ice for half an hour. Centrifuged (20000×g) to remove the cell debris, the supernatant was kept, and the total protein content in the supernatant was detected.

3.3 The specific step total protein in vitro propionylation derivatized reaction and protein enzymolyzed total protein in vitro propionylation derivatized reaction are as follow:

1) Section 1.2 ion each cell line protein extract supernatant, where each of supernatant containing 20 mg total protein to prepare propionylated reaction;

2) To the supernatant containing high protein 200 μL of propionic anhydride was added, vortexed well, an appropriate amount of volume 2 M NaOH was added, the pH was adjusted to 8.0, and reacted at room temperature for one hour.

3) Step 2 was repeated once. Again, 200 μL of propionic anhydride was added to the solution of Step 2, mixed well, an appropriate amount of volume of 2 M NaOH was added, the pH was adjusted to 8.0, and reacted at room temperature for two hours.

4) after completion of the reaction, 10 μL of ethanolamine was added at room temperature 30 minutes, to terminate the propionylation reaction of Step 3.

5) to the solution of Step 4, trichloroacetic acid (TCA) was dropwisely added to a final concentration of 20% (v/v), shaken gently, precipitated at 4° C. overnight.

6) on the next day, centrifuged at 16,000×g at 4° C. for 10 minutes, and the supernatant was discarded.

7) a 4° C. pre-cooled acetone protein precipitated was added, and centrifuged under 16000×g at 4° C. for 10 minutes, the supernatant was discarded.

8) Step 7 was repeated twice.

9) 2 mL of 100 mM ammonium hydrocarbonate was added, the protein precipitated in Step 8 under pH=8 was resuspended.

10) At a ratio of 1:50 (w/w) of trypsin with protein precipitated substrate, an appropriate amount of trypsin was added to above-described protein solution, and enzymolyzed at 37° C. in a thermostatic water bath overnight.

11) On the next day, centrifuged, and dithiothreitol (DTT) was added to a final concentration of 5 mM, and reacted in a 55° C. thermostatic water bath for 30 minutes.

12) Centrifuged, and a fresh prepared iodoacetamide water solution was added to a final concentration of 15 mM, reacted at room temperature in the dark for 30 minutes.

13) After completion of the reaction, centrifuged, and 0.72 M cysteine was added to a final concentration of 30 mM, and reacted at room temperature for 30 minutes.

14) At a ratio of 1:100 (w/w) of trypsin with substrate, and an appropriate amount of trypsin was added, enzymolyzed at 37° C. in a thermostatic water bath for three hours, then desalted in $^{18}C$ column, polypeptide components were separated by HPLC.

Example 4: Polypeptide Component Separation Based on HPLC

Before affinity purification, the propionylation derivatized trypsin peptide Example 1 obtain from each sample was separated by HPLC. The separation method was as follow: What was used in this separation is Varian SD1 LC (Agilent Technologies, CA) and Xbridge C18 (19×150 cm; Waters, Mass.), using 2 to 40% buffer B (10 mM ammonia water or 80% ACN, pH=8.5), the gradient was set to 70 minutes, at a flow rate of 10 ml/min elution. The sample was collected at equal time interval, totally 60 components were collected (about 10 ml/tube), then combined to 20 components. Each component of all 20 components was withdrawn to dryness respectively by a vacuum concentrator (ThermoFisher).

Example 5: Preparation of Lysine Propionyl Methylated Pan Antibody Coupled Resin and Affinity Enrichment of the Modified Polypeptide Preparation of lysine propionyl methylation pan antibody coupled resin: 1 ml of protein A agarose resin (Life Technologies, CA) pre-cooled phosphate buffer solution (PBS) washed three times, then 4 mg of lysine propionyl methylated pan antibody (in 2 ml of pre-cooled phosphate buffer solution) incubated at 4° C. for 4 hours; centrifuged at 500×g for 30 s, then the antibody-protein A agarose resin was washed with a pre-cooled phosphate buffer for three times to remove the unbonded antibody, to prepare the lysine propionyl methylated pan antibody coupled resin.

The antibody used in the present embodiment was the antibody prepared by specific embodiment 1 or 2 of the present invention.

Affinity enrichment of the modified polypeptide: the enzymolyzed polypeptide (2 mg) obtained in Example 2 was dissolved in 200 ul of pre-cooled NETN buffer solution (100 mM NaCl, 1 mM EDTA, 20 mM Tris pH 8.0 and 0.5% (w/v) NP-40), then 20 ul of lysinepropionyl methylation pan antibody coupled resin was added, incubated at 4° C. overnight. Centrifuged at 500×g for 30 s, affinity enriched polypeptide-antibody-protein A agarose resin was washed with a NETN buffer for three times, then washed with ddH$_2$O twice. The polypeptide affinity enriched by antibody-protein A agarose resin was eluted with 100 ul of 0.1% trifluoroacetic acid (TFA) totally three times. The diluents were combined for three times, drawn day by a vacuum concentrator for use in subsequent mass spectrum analysis.

Example 6: Retrieving Protein Sequence Via HPLC-MS/MS Analysis and Database

Ionization of elution peptide: the propionyl methylation peptides enriched in Example 3 (peptides of 20 components) were dissolved in 3 µl of HPLC buffer A (0.1% formic acid in water, v/v) then successively into a capillary RPLC trap column (100 µm inner diameter ×2 cm, Luna C18 filled, 5 µm, pore size 100 Å, China Dima) and maximum pressure of 250 par automatic sampler, buffer solution was 100% buffer solution A (0.1% FA water solution of HPLC grade). After the sample was charged and completion of elution, peptide was transferred to fill an analytic column (10 cm of length, 75 µm of ID) filled with C18 resin (3-µm particle size, 90-Å pore size, China Dima), and the analytic column is linked to EASY-nLC 1000 HPLC system (Thermo Fisher Scientific Inc, MA).

Mass spectrum analysis: the elute peptide was ionized, then introduced into LTQ Orbitrap EliteMass Spectrometer (Thermo Fisher Scientific Inc, MA) by nano-spray.at R=24,000 and m/z 400 resolution, whole range mass spectrometry scan (from m/z 300 to m/z 2,000). 10 types of highest abundance ions in were separates in Linear Ion Trap, by corrosion then split (CID), this normalization is 35%. The limiting interval un-related with to data is 30 seconds, repetitive count is 2, eliminating window setting of +2 Da and −1 Da. The HPLC-MS/MS date obtained was analyzed using Mascot (v2.3, Matrix Science, UK). Peak is passed through extract_msn.exe software of Thermo Fisher. Mascot analysis ion mass error was set as ±10 ppm, fragment mass error was set to ±0.6 Da. The obtained data were reached in UniPort Human (88,817 sequences) database, and parameters were set as follows: fixed modification is set as cysteine residues urea methylation, variable modification pf the low mass peptide was $^{13}$CD$_3$-methionine, $^{13}$CD$_3$-methionine oxidization, lysine propionylation (lysine+56.0262), lysine propionyl $^{13}$CD$_3$-methylation (lysine+74.0640) and lysine propionyl-methyl-methylation (lysine+70.0418). All of the mass spectrometry data use and manual verification with mascot ion score were higher than 20.

Example 7: Purification of the CDCL1 Protein in K562 Cells $^{13}$CD$_3$-methionine re-labeled K562 cells were dissolved in 1×NETN buffer (100 mM NaCl, 1 mM EDTA, 20 mM Tris pH 8.0 and 0.5% w/v, NP-40). The cell homogenate was centrifuged at 12,000×g at 4° C. for 10 minutes to remove cell debris.

To the lysate, anti-CDC5L antibody (Santa Cruz, Tex.) was added at 4° C. overnight, then protein A/G agarose resin (Santa Cruz, Tex.) was added at 4° C. and incubated for 4 hours. After washing of the non-specifically bonded protein, the immunized precipitate was separated in 4-12% SDS-PAGE (Life Technologies, CA) after pyrolysis in the loading buffer solution. The gel strip corresponding to the target protein was cut down and enzymolyzed in the gel, then the enzymolyzed peptide was dissolved in 0.1% TFA buffer and introduced into HPLC-MS/MS mass spectrometry of Example 6 for analysis.

Example 8: Preparation of the Total Protein in Liver Cancer Sample

The liver cancer tissue was acquired from a liver cancer patient under operation in Zhongshan Hospital (China, Shanghai), and the study content has been informed to the patient or donor. The fresh tissue cut down was rapidly frozen with liquid nitrogen before further treatment. Before extracting the protein, the liver tissue was cut rapidly using a surgical scissors and the blood was washed off using a pre-cooled phosphate buffer (PBS). The tissue placed in the pre-cooled PBS was stirred to evenly by a stirrer, the connective tissue was filtered off by a filter (70 µM pore size). The liver cancer cells were obtained by centrifugation, and cell culture and labelling were conducted according to method of Section 1.1 in Example 1, cultured in a cell culture medium and labelled with $^{12}$CH$_2$-methionine or $^{13}$CD$_2$-methionine. After cell labelling extraction of the total protein and propionylation reaction were conducted by the method of 1.2 and 1.3 Section in Example 1, at the same time according to the same method by enzyme to separate, the degree of propionylation reaction was analyzed by chromatography, result indicate that in the protein of these cell, only very small amount of the peptide didn't undergo the propionylation reaction, essentially all proteins underwent the propionylation reaction.

Result 1

Taking HeLa cell for example, according to the method of above-described Example 1-4 identify the presence lysine monomethylation modification in HeLa cell line and the modification site, it is required to combine $^{13}$CD$_3$ methionine labelling method with SILAC method. During experiment, the HeLa cell lines are respectively cultured in a culture medium containing $^{12}$CH$_3$-methionine and $^{13}$CD$_3$ methionine. When the cell labelling is complete and required amount was reached, respectively collect cell extract total protein, then same amount of two lysis protein were mixed and in vitro propionylation derivatization reaction was conducted, trypsin digestion to produce enzymolyzed polypeptide, by preparative HPLC separate polypeptide to produce 20 polypeptide components. Each of Separate polypeptide component were enriched by the lysinepropionyl methylated pan antibody, then by nano-HPLC/MS/MS analysis (detailed analytical method is seen in Example 6).

During mass spectrum analysis, propionyl methylation modification, polypeptide methyl group hydrogen ion and carbon ion were replaced, this will induce 4.002 Daltons of mass displacement (Figure A). To ensure the accuracy of the analysis, all Mascot MS/MS spectrum further by manual check. Using such a method, 183 propyl methylated modified polypeptide of high confidence were identified from HeLa cells, indirectly demonstrating the presence of HeLa cell 183 monomethylated modified lysine. By manual check of the original data, where, 180 propyl methylation modification polypeptides have a pair of precursor ion, corresponding 190 methylation modification sites of 162 types proteins (FIG. 3C). Only two polypeptides contain "heavy" ion, and one polypeptide contain "light" ion.

This sufficiently demonstrates that the method of $^{13}CD_3$ replacing methyl group is used in monometylation site analysis and eliminate the false positive result was reliable. It also demonstrated that such method used in identifying the monomethyl modified polypeptide is reliable.

Result 2

Using $^{13}CD_3$ methionine labelling method to detect K562 cells (chronic myeloid leukemia cells), SW620 cells (Colon cancer cells), A549 cells (lung cancer cells) and SMM7721 cells (liver cancer cells) and other 4 types of human-derived tumor cells lysine monomethylation modification, specific step as described in Example 1-4 step and condition where polypeptide identification using MASCOT algorithm and 1% false positive rate, eliminate the record of MASCOT score lower than 20, using a stringent criteria, manually check each diagram (as above described)22. Totally identified 48 non-redundant monomethylated polypeptide, corresponding to 460 sites in 403 proteins. In these identified polypeptide, 73% of MASCOT score higher than 30 (FIG. 10A). By retrieving the public Uniprot protein database, the identified most monomethyltion sites by the present invention has not been reported.

Monomethyl sinepolypeptide and protein identified by the present invention can be seen in the attached table (FIG. 13). This indicate, by using the method of the present invention can accurately identify monomethyl lysine polypeptide and protein identified by other methods, and meanwhile identify many previously un-identified other monomethyl lysine polypeptide and protein. FIG. 13 indicates in five tumor cell lines 29 lysine monomethylation modified proteins and modification sites were identified.

As known from above identification results, by using the method of the present invention, lysine modification of those previous unknown monomethylation modification can be identified. For example, on the STUB1 gene-encoded protein substrate, the present invention detected the presence of lysine monomethylation modification on the lysine (K2) at the second position, but the lysine monomethylation modification at this site has not been reported.

The lysine monomethylation of the core histone has been studied extensively, thus is can be used as a good positive control. In agreement with prediction, the present invention method totally identified the lysine monomethyllation sites of 12 core histones. Besides that, several methylation sites of the extensively studied histones H3K4, H3K9, H3K27, H3K36, H3K79 and histone H4K20 were identified, monomethylation site of histone H3K18 which has not almost been studied were identified. Because these five cells contain most of these monomethylation modification sites, it reveals that such detection method of lysine monomethylation modification is stable and reliable. Moreover, the method of the present invention also identified some new modification sites from many known monomethylated modified proteins. For example, in WIZ protein, besides that the reported K976 site was identify, the present invention also identified two new monometylation sites of K1321 and K1463 (FIG. 13).

Result 3

In order to validate the reliability of the present invention method, taking $^{13}CD_3$-Met labeled K562 cells for example, by the method of the present invention, the presence of monomethylation modification at K114 site of CDC5L protein of K562 cells was identified. The sequence of one polypeptide obtained after in vitro propionylation reaction and enzyme digestion to the total protein of K562 cells via is LANTQGK*$_{pr+me}$K$_{pr}$AK$_{pr}$R (SEQ ID NO:5) (K*$_{pr+me}$ represents the propionyled monomethylated lysine, K$_{pr}$ means lysine is also linked with propionyl group). As known from above description, before the in vitro propionylation reaction to this peptide sequence was not conducted, this polypeptide sequence in biological cell or tissue should be: LANTQGK$_{me}$* KAKR (SEQ ID NO:29) (K* indicates that occurrence of the monomethylation modification at this site, i.e. 114th site). In order to validate this conclusion, the inventors conducted tandem mass spectrum analysis for the artificially synthesized LANTQGK*$_{pr+me}$K$_{pr}$AK$_{pr}$R (SEQ ID NO:5). The result indicates that the synthetic polypeptide has completely same MS/MS secondary spectrum as the LANTQGK*$_{pr+me}$K$_{pr}$AK$_{pr}$R (SEQ ID NO:5) polypeptide identified from cells, but there is a 4 Da of mass displacement on the corresponding b-,y-ion (FIG. 11A).

In order to further validate real occurrence of cell in vivo lysine monomethylation modification at this site, the present invention also use cell labelling in vivo CDC5L protein purification identify lysine monomethylation modification artificially synthesized polypeptide tandem mass spectrum analysis. LANTQGK$^{13}$$_{CD3}$-meKAK polypeptide was identified in the purified CDC5L protein. The mass spectrum analysis of the artificially synthesized LANTQGK$_{12CH3-me}$KAK polypeptide indicate, the MS/MS secondary spectrum of this polypeptide identical with LANTQGK$^{13}$CD$_3$-meKAK identified in the purified CDC5L protein, there is a 4 Da mass displacement on 13CD3-labeled corresponding b-, y-ion, thereby demonstrating reliability of lysine monomethylation modification identified in CDC5L protein.

The identification of lysine monomethyl modification in human liver cancer tissue further validates reliability of the method of the present invention. Compared with the lysine monomethylation modification data identified in above-described five types of cells, 32 monomethylation sites in 5 types of cells of 29 monomethylated modified polypeptides identified in liver cancer tissue includes 20 new methylation sites and 6 histone H3 lysine monomethylation modification sites (FIGS. 10B and 13).

Discussion

Although the proteomics approach based on affinity enrichment recently has been utilized in identification of many methylated peptide of cell lysate, there is also challenge, especially the monomethylation modification indus minor change in the physicochemical property makes it difficult to be identified by the conventional lysine monomethylated antibody enrichment method. By the method of the present invention, the inventor has identified 460 lysine monomethylation sites in 403 substrate proteins, this represents the maximum data of current lysine monomethylation. This result clearly confirms the effectiveness and reliability of the method of the present invention.

Although it is very effective to the lysine monomethylation, our method is not suitable for the level detection of lysine di-methylation and tri-methylation, because these two modified amino acid residues cannot react with propionyl anhydride. We also improved the precision of detection to the monomethylated peptide by the $^{13}CD_3$-methionine labelling approach. However, such method cannot be directly used in clinical tissue sample, the reliability of polypeptide identification may also be resolved by alternative methods, such as strict manual verification and MS/MS analysis of the synthetic polypeptide.

In recent years, the biological reaction of the protein lysine monomethylation aroused wide concern of study organizations. The protein lysine methylation enzymes have been used as potential drug targets of different diseases. Moreover, inhibitors of some lysine methylation regulatory enzymes are now clinically evaluated. However, the existing knowledge on the lysine monomethylation is merely limited to a limited number of proteins, such as histone and p53, this limits the application of lysine monomethylation modification in basic medicine study or even drug development fields. Our research not only provides an effective high-throughput identification method for the lysine monomethylated substrate, furthermore expands the known list of the lysine monomethylated protein. By combing the proteomics method described by the present invention with genetic manipulation expressed by the methylation enzymes, the invention may be utilized in identifying of the substrate of methyltransferase and demethylase, and dynamic analysis of methylation substrate under diseases condition. Moreover, the lysine monomethylatyion modification provided by the present invention will be a meaningful start point for further biological study, so as to realize function characteristic description of lysine monomethylated protein and interpretation for diseases specific lysine monomethylation pathway.

Those skilled in the art should realize that many methods can be used to produce the antibody or bonded fragment of the present invention, and in term of the screening and selection of affinity and specificity of various polypeptides, these methods do not change the gist of the present invention. Those skilled in the art will easily appreciate that the present invention is suitable for the objects obtained, also include inherent results and advantages. The examples referred here are preferred examples, having exemplary purpose, but the present invention has no any limitation to the range of present invention. Clearly, those skilled in the art of the present invention can make different replacements and modifications without departing from the scope and spirit of the present invention. All the patents and publications referred in the present invention specification all indicate these are the disclosed technology in the art, the present invention can be utilized. All patents and publications cited here are all likewise listed in the reference, it is same as each publication being individually be referred and cited. Here said the present invention can be achieved without any one or more elements, one or more restrictions, here there is no special illustration to such restriction. For example, here in each of example, the term "include", "essentially be composed of . . . " and "be composed of . . . " can be replaced by the other 2 terms except one of the two terms. Here term and expression, here it is not intended to point out these terms and explanations described in this specification excludes any equivalent features, but it is to be noted that any suitable changes or modifications can be made within the scope of the present invention and the claims. It can be understood that the examples described in the present invention are all some preferred examples and characteristics, any person skilled in the art can make some alterations and changes under the gist described by the present invention, these alterations and changes are also deemed to belong to the scope of the present invention and the scope defined by the independent claims and dependent claims. Other embodiments are included in the flowing claims.

REFERENCE

1. Cheng X1, Zhang X. Structural dynamics of protein lysine methylation and demethylation. *Mutat Res.* 618, 102-15 (2007);
2. Kondo Y1, Shen L, Issa J P. Critical role of histone methylation in tumor suppressor gene silencing in colorectal cancer). *Mol Cell Biol.* 23, 206-15(2003);
3. Berdasco M1, Ropero S, et al., Epigenetic inactivation of the Sotos overgrowth syndrome gene histone methyltransferase NSD1 in human neuroblastoma and glioma). *Proc Natl Acad Sci USA.* 106, 21830-5(2009);
4. Kouzarides T. Chromatin modifications and their function. *Cell.* 128, 693-705(2007);
5. Berger S L. The complex language of chromatin regulation during transcription. *Nature.* 447, 407-12(2007).
6. Barski Al, Cuddapah S, et al., High-resolution profiling of histone methylations in the human genome). *Cell.* 129, 823-37(2007);
7. Rea S1, Eisenhaber F, O'Carroll D, et al., Regulation of chromatin structure by site-specific histone $H_3$ methyltransferases). *Nature.* 406, 593-9(2000);
8. Liang Z1, Wong R P, et al., Development of pan-specific antibody against trimethyllysine for protein research. *Proteome Sci.* 6:2 (2008);
9. Fmoc Solid Phase Peptide Synthesis—A Practical Approach). Oxford University Express, 2000;
10. Making AND Using Antibodies-A practical handbook). CRC Press, 2007;
11. Bird RE1, Hardman K D, et al., Single-chain antigen-binding proteins). *Science.* 242, 423-6(1988);
12. Huston JS1, Levinson D, et al., Protein engineering of antibody binding sites: recovery of specific activity in an anti-digoxin single-chain Fv analogue produced in *Escherichia coli. Proc Natl Acad Sci USA.* 85, 5879-83 (1988).
13. Cheng X1, Zhang X. Structural dynamics of protein lysine methylation and demethylation. *Mutat Res.* 618, 102-15(2007);
14. Kondo Y1, Shen L, Issa J P. Critical role of histone methylation in tumor suppressor gene silencing in colorectal cancer. *Mol Cell Biol.* 23, 206-15(2003);
15. Berdasco M1, Ropero S, et al., Epigenetic inactivation of the Sotos overgrowth syndrome gene histone methyltransferase NSD1 in human neuroblastoma and glioma). *Proc Natl Acad Sci USA.* 106, 21830-5(2009);
16. Kouzarides T. Chromatin modifications and their function. *Cell.* 128, 693-705(2007);
17. Berger S L. The complex language of chromatin regulation during transcription). *Nature.* 447, 407-12(2007).
18. Barski Al, Cuddapah S, et al., High-resolution profiling of histone methylations in the human genome). *Cell.* 129, 823-37(2007);
19. Rea S1, Eisenhaber F, O'Carroll D, et al., Regulation of chromatin structure by site-specific histone H3 methyltransferases). *Nature.* 406, 593-9(2000);

20. Liang Z1, Wong R P, et al., Development of pan-specific antibody against trimethyllysine for protein research. *Proteome Sci.* 6:2 (2008);
21. Fmoc Solid Phase Peptide Synthesis—A Practical Approach. Oxford University Express, 2000;
22. Making AND Using Antibodies-A practical handbook). CRC Press, 2007;
23. Bird RE1, Hardman K D, et al., Single-chain antigen-binding proteins). *Science.* 242, 423-6(1988);
24. Huston JS1, Levinson D, et al., Protein engineering of antibody binding sites: recovery of specific activity in an anti-digoxin single-chain Fv analogue produced in *Escherichia coli*). *Proc Natl Acad Sci USA.* 85, 5879-83 (1988).
25. Copeland, R. A., Moyer, M. P. & Richon, V. M. Targeting genetic alterations in protein methyltransferases for personalized cancer therapeutics. *Oncogene* 32, 939-946 (2013).
26. Martin, C. & Zhang, Y The diverse functions of histone lysine methylation. *Nature reviews. Molecular cell biology* 6, 838-849 (2005).
27. Schapira, M. Structural Chemistry of Human SET Domain Protein Methyltransferases. *Current chemical genomics* 5, 85-94 (2011).
28. Pedersen, M. T. & Helin, K. Histone demethylases in development and disease. *Trends in cell biology* 20, 662-671 (2010).
29. Greer, E. L. & Shi, Y Histone methylation: a dynamic mark in health, disease and inheritance. *Nature reviews. Genetics* 13, 343-357 (2012).
30. Arrowsmith, C. H., Bountra, C., Fish, P. V., Lee, K. & Schapira, M. Epigenetic protein families: a new frontier for drug discovery. *Nature reviews. Drug discovery* 11, 384-400 (2012).
31. Allfrey, V. G, Faulkner, R. & Mirsky, A. E. Acetylation and Methylation of Histones and Their Possible Role in the Regulation of RNA Synthesis. *Proc Natl Acad Sci USA* 51, 786-794 (1964).
32. Vidali, G, Gershey, E. L. & Allfrey, V. G Chemical studies of histone acetylation. The distribution of epsilon-N-acetyllysine in calf thymus histones. *J Biol Chem* 243, 6361-6366 (1968).
33. Gu, W. & Roeder, R. G Activation of p53 sequence-specific DNA binding by acetylation of the p53 C-terminal domain. *Cell* 90, 595-606 (1997).
34. Gu, W., Luo, J., Brooks, C. L., Nikolaev, A. Y & Li, M. Dynamics of the p53 acetylation pathway. *Novartis Found Symp* 259, 197-205; discussion 205-197, 223-195 (2004).
35. Choudhary, C. et al. Lysine acetylation targets protein complexes and co-regulates major cellular functions. *Science* 325, 834-840 (2009).
36. Zhao, S. et al. Regulation of cellular metabolism by protein lysine acetylation. *Science* 327, 1000-1004 (2010).
37. Chen, Y et al. Quantitative acetylome analysis reveals the roles of SIRT1 in regulating diverse substrates and cellular pathways. *Mol Cell Proteomics* 11, 1048-1062 (2012).
38. Ficarro, S. B. et al. Phosphoproteome analysis by mass spectrometry and its application to *Saccharomyces cerevisiae*. *Nature biotechnology* 20, 301-305 (2002).
39. Ong, S. E., Mittler, G & Mann, M. Identifying and quantifying in vivo methylation sites by heavy methyl SILAC. *Nature methods* 1, 119-126 (2004).
40. Zhang, Z. et al. Identification of lysine succinylation as a new post-translational modification. *Nat Chem Biol* 7, 58-63 (2011).
41. Garcia, B. A. et al. Chemical derivatization of histones for facilitated analysis by mass spectrometry. *Nature protocols* 2, 933-938 (2007).
42. Chen, Y et al. Lysine propionylation and butyrylation are novel post-translational modifications in histones. *Mol Cell Proteomics* 6, 812-819 (2007).
43. http://www.unimod.org/modifications_list.php?
44. Park, J. et al. SIRT5-mediated lysine desuccinylation impacts diverse metabolic pathways. *Mol Cell* 50, 919-930 (2013).
45. Chen, Y, Kwon, S. W., Kim, S. C. & Zhao, Y Integrated approach for manual evaluation of peptides identified by searching protein sequence databases with tandem mass spectra. *Journal of proteome research* 4, 998-1005 (2005).
46. Garcia, B. A. et al. Organismal differences in post-translational modifications in histones H3 and H4. *J Biol Chem* 282, 7641-7655 (2007).
47. Moore, K. E. et al. A general molecular affinity strategy for global detection and proteomic analysis of lysine methylation. *Mol Cell* 50, 444-456 (2013).
48. Boudrez, A. et al. NIPP1-mediated interaction of protein phosphatase-1 with CDC5L, a regulator of pre-mRNA splicing and mitotic entry. *J Biol Chem* 275, 25411-25417 (2000).
49. Clarke, S. G Protein methylation at the surface and buried deep: thinking outside the histone box. *Trends in biochemical sciences* 38, 243-252 (2013).
50. Jensen, L. J. et al. STRING 8—a global view on proteins and their functional interactions in 630 organisms. *Nucleic acids research* 37, D412-416 (2009).
51. Ruepp, A. et al. CORUM: the comprehensive resource of mammalian protein complexes. *Nucleic acids research* 36, D646-650 (2008).
52. http://www.uniprot.org/.
53. Musselman, C. A., Lalonde, M. E., Cote, J. & Kutateladze, T. G Perceiving the epigenetic landscape through histone readers. *Nature structural & molecular biology* 19, 1218-1227 (2012).
54. Bothwell, I. R. et al. Se-adenosyl-L-selenomethionine cofactor analogue as a reporter of protein methylation. *Journal of the American Chemical Society* 134, 14905-14912 (2012).
55. Liu, H. et al. A Method for Systematic Mapping of Protein Lysine Methylation Identifies Functions for HP1beta in DNA Damage Response. *Mol Cell* 50, 723-735 (2013).
56. Witze, E. S., Old, W. M., Resing, K. A. & Ahn, N. G Mapping protein post-translational modifications with mass spectrometry. *Nature methods* 4, 798-806 (2007).
57. Wagner, T. & Jung, M. New lysine methyltransferase drug targets in cancer. *Nature biotechnology* 30, 622-623 (2012).
58. Wang, Y et al. Reversed-phase chromatography with multiple fraction concatenation strategy for proteome profiling of human MCF10A cells. *Proteomics* 11, 2019-2026 (2011).
59. Li, J. et al. Identification and characterization of nardilysin as a novel dimethyl H3K4-binding protein involved in transcriptional regulation. *J Biol Chem* 287, 10089-10098 (2012).
60. Ashburner, M. et al. Gene ontology: tool for the unification of biology. The Gene Ontology Consortium. *Nature genetics* 25, 25-29 (2000).

61. Kanehisa, M. & Goto, S. KEGG: kyoto encyclopedia of genes and genomes. *Nucleic acids research* 28, 27-30 (2000).
62. Finn, R. D. et al. The Pfam protein families database. *Nucleic acids research* 36, D281-288 (2008).
63. Huang da, W., Sherman, B. T. & Lempicki, R. A. Bioinformatics enrichment tools: paths toward the comprehensive functional analysis of large gene lists. *Nucleic acids research* 37, 1-13 (2009).
64. Hochberg, Y. B. a. Y Controlling the False Discovery Rate: A Practical and Powerful Approach to Multiple Testing. *Journal of the Royal Statistical Society. Series B*57, 12 (1995).
65. Shannon, P. et al. Cytoscape: a software environment for integrated models of biomolecular interaction networks. *Genome research* 13, 2498-2504 (2003).
66. Bader, G D. & Hogue, C. W. An automated method for finding molecular complexes in large protein interaction networks. *BMC bioinformatics* 4, 2 (2003).

I claim:

1. An antibody, wherein the antibody is an antibody produced by PMT-001 cell strain with a preservation number of CGMCC NO.9109.

* * * * *